(12) United States Patent
Kuroda et al.

(10) Patent No.: US 9,155,551 B2
(45) Date of Patent: Oct. 13, 2015

(54) TREATMENT INSTRUMENT

(71) Applicant: OLYMPUS MEDICAL SYSTEMS CORP., Tokyo (JP)

(72) Inventors: Noriko Kuroda, Tokyo (JP); Ken Yamatani, Tokyo (JP); Takuo Yokota, Tokyo (JP); Masatoshi Tonomura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/858,243

(22) Filed: Apr. 8, 2013

(65) Prior Publication Data

US 2013/0317515 A1 Nov. 28, 2013

Related U.S. Application Data

(63) Continuation of application No. PCT/JP2012/065424, filed on Jun. 15, 2012.

(60) Provisional application No. 61/513,899, filed on Aug. 1, 2011.

(51) Int. Cl.
*A61B 17/24* (2006.01)
*A61B 17/221* (2006.01)
(Continued)

(52) U.S. Cl.
CPC ........... *A61B 17/221* (2013.01); *A61B 10/0266* (2013.01); *A61B 17/22031* (2013.01);
(Continued)

(58) Field of Classification Search
CPC ........... A61B 17/221; A61B 17/22031; A61B 17/32056; A61B 2017/2212; A61B 2017/00287; A61B 10/0266; A61B 10/06; A61B 17/32053; A61B 17/3478; A61B 17/320016; A61B 2017/2911; A61B 2017/2938; A61B 2017/320064; A61B 2017/2937; A61B 2017/32044; A61B 2017/320008; A61B 2017/2215; A61B 2017/2926; A61B 2017/320012; A61B 2017/22079; A61B 2017/00278; A61B 2217/005; A61B 1/0014; A61B 2019/4889
USPC .......................... 606/113, 114, 127, 151, 200
See application file for complete search history.

(56) References Cited

U.S. PATENT DOCUMENTS 8,092,470 B2   1/2012 Miyamoto et al.
8,425,533 B2 *  4/2013 Parihar et al. ................. 606/127
(Continued)

FOREIGN PATENT DOCUMENTS

JP   A-10-137252    5/1998
JP   A-2005-511192  4/2005
(Continued)

OTHER PUBLICATIONS

International Search Report issued in International Patent Application No. PCT/JP2012/065424 dated Jul. 31, 2012 (w/ translation).
(Continued)

*Primary Examiner* — Tuan V Nguyen
*Assistant Examiner* — Tin Nguyen
(74) *Attorney, Agent, or Firm* — Oliff PLC

(57) ABSTRACT

A treatment instrument has a longitudinal-axis member having a longitudinal axis, a curved portion formed on a distal end side of the longitudinal-axis member, a lumen formed along the longitudinal axis of the longitudinal-axis member, and a through hole that communicates with the lumen, and opens toward the inner side of a curve of the curved portion when the curved portion is curved.

10 Claims, 33 Drawing Sheets

(51) Int. Cl.
*A61B 17/22* (2006.01)
*A61B 17/34* (2006.01)
*A61B 17/3205* (2006.01)
*A61B 10/02* (2006.01)
*A61B 17/00* (2006.01)
*A61B 17/29* (2006.01)
*A61B 17/32* (2006.01)
*A61B 19/00* (2006.01)
*A61B 1/00* (2006.01)
*A61B 10/06* (2006.01)

(52) U.S. Cl.
CPC ..... *A61B17/32053* (2013.01); *A61B 17/32056* (2013.01); *A61B 17/3478* (2013.01); *A61B 1/0014* (2013.01); *A61B 10/06* (2013.01); *A61B 17/320016* (2013.01); *A61B 2017/00278* (2013.01); *A61B 2017/2215* (2013.01); *A61B 2017/22079* (2013.01); *A61B 2017/2911* (2013.01); *A61B 2017/2926* (2013.01); *A61B 2017/2937* (2013.01); *A61B 2017/2938* (2013.01); *A61B 2017/320008* (2013.01); *A61B 2017/320012* (2013.01); *A61B 2017/320044* (2013.01); *A61B 2017/320064* (2013.01); *A61B 2019/4889* (2013.01); *A61B 2217/005* (2013.01)

(56) References Cited

U.S. PATENT DOCUMENTS

| 2001/0002437 A1 | 5/2001 | Pagedas |
| 2003/0109889 A1* | 6/2003 | Mercereau et al. ........... 606/127 |
| 2006/0058776 A1* | 3/2006 | Bilsbury ...................... 604/540 |
| 2011/0184431 A1* | 7/2011 | Parihar et al. ................. 606/114 |
| 2011/0184433 A1 | 7/2011 | Parihar et al. |
| 2011/0184436 A1 | 7/2011 | Shelton, IV et al. |

FOREIGN PATENT DOCUMENTS

| JP | A-2005-529668 | 10/2005 |
| JP | A-2007-534451 | 11/2007 |
| JP | A-2009-523054 | 6/2009 |
| WO | WO 03/049625 A1 | 6/2003 |
| WO | WO 2007/081601 A2 | 7/2007 |

OTHER PUBLICATIONS

Japanese Office Action issued in Japanese Patent Application No. 2013-515603 dated Jun. 18, 2013 (w/translation).

Mar. 4, 2015 Extended European Search Report issued in International Application No. 12820457.5.

* cited by examiner

TREATMENT INSTRUMENT

This application is a continuation application based on U.S. Patent Application No. 61/513,899, provisionally applied in the United States on Aug. 1, 2011, and International Application No. PCT/JP2012/065424, filed on Jun. 15, 2012. The contents of both the United States Patent Application and the PCT Application are incorporated herein by reference.

BACKGROUND OF THE INVENTION

1. Field of the Invention

The present invention relates to a treatment instrument.

2. Description of Related Art

In the related art, a procedure of endoscopically excising a lesion or the like is known. As a treatment instrument to be used in such a procedure, a treatment instrument used together with an endoscope apparatus in collecting the excised lesion is known. For example, a tissue collecting tool having a distal end collection section formed in a basket shape by a plurality of basket wires is disclosed in Japanese Unexamined Patent Application, First Publication No. H10-137252. The tissue collecting tool described in Japanese Unexamined Patent Application, First Publication No. H10-137252 is able to expand two basket wires that constitute the distal end collection section, thereby containing a lesion or the like within the distal end collection section through a gap between the expanded basket wires.

In the related art, as a treatment instrument to be used to collect the excised lesion or the like, cup-type forceps, basket-type forceps, or the like is used. In the treatment instrument of the cup-type forceps or basket-type forceps that are used in the related art, the size of the treatment instrument is limited to a size capable of being inserted through a treatment instrument channel of a flexible endoscope. For this reason, in the above treatment instrument, the size of a cup or a basket should have a much smaller volume than a volume capable of raking out all necrotic tissues at one time.

An object of the invention is to provide a treatment instrument that can collect tissue more efficiently than the cup-type forceps or basket-type forceps of the related art while adhering to limitation of dimensions and is capable of being inserted through a treatment instrument channel.

SUMMARY OF THE INVENTION

According to a first aspect of the invention, a treatment instrument includes a longitudinal-axis member that is tubular and is provided so as to extend along a longitudinal axis; a collecting member that is provided at a distal end of the longitudinal-axis member and has an opening portion for introducing a tissue and a containing portion including an internal space for containing the tissue in communication with the opening portion; a frame part that is provided along an edge of the opening portion in order to define a shape of the opening portion, has a proximal end portion capable of being housed inside the longitudinal-axis member, and operates so that the opening portion is closed when the proximal end portion is housed inside the longitudinal-axis member; an opening operating member that is connected to the proximal end portion of the frame part and is provided so as to be capable of moving inside the longitudinal-axis member along the longitudinal axis; a curved portion that has a first end portion fixed to a distal end portion of the frame part and a second end portion connected to the first end portion and provided to extend toward the proximal end portion of the frame part, the curved portion being formed in a curved shape along the containing portion from the first end portion to the second end portion; an operating member that is connected to the second end portion of the curved portion; and an operation portion that allows the opening operating member to move relative to the longitudinal-axis member and the operating member so that the proximal end portion of the frame part is pulled into the longitudinal-axis member.

According to a second aspect of the invention, in the above first aspect, the curved portion may be a volume adjusting member that has a portion passing through a deepest portion of the containing portion, is formed in a curved shape through the deepest portion, and adjusts a volume of the containing portion, and the operating member may be a volume operating member that is provided so as to be movable along the longitudinal axis with respect to the opening operating member.

According to a third aspect of the invention, in the above second aspect, the operation portion may advance and retract the opening operating member and the volume operating member in the direction of the longitudinal axis independently from each other.

According to a fourth aspect of the invention, in the above second aspect, the depth of the containing portion when being measured in a direction intersecting an opening surface defined by the edge of the opening portion, and an opening area of the opening portion may be adjusted independently from each other by advancing and retracting the opening operating member and the volume operating member independently from each other in the direction of the longitudinal axis.

According to a fifth aspect of the invention, in the above fourth aspect, the treatment instrument may have a state where the opening portion is closed when the depth is maintained.

According to a sixth aspect of the invention, in the above second aspect, the treatment instrument may have a state where the position of the opening operating member with respect to the longitudinal-axis member is fixed and the volume operating member is advanced and retracted with respect to the longitudinal-axis member whereby the volume of the containing portion varies while the opening area of the opening portion is maintained at a predetermined opening area, and a state where the position of the volume operating member with respect to the longitudinal-axis member is fixed and the opening operating member is advanced and retracted with respect to the longitudinal-axis whereby the opening area of the opening portion varies while the depth of the containing portion is maintained.

According to a seventh aspect of the invention, in the above sixth aspect, the treatment instrument may have a state where the opening portion is closed when the depth is maintained.

According to an eighth aspect of the invention, in the above fifth or seventh aspect, the longitudinal-axis member may be a flexible structure.

According to the treatment instruments of the above respective aspects, in comparison with the cup-type forceps or basket-type forceps of the related art, a tissue can be collected more efficiently under the limitation of dimensions capable of being inserted through the treatment instrument channel.

DETAILED DESCRIPTION OF THE INVENTION

First Embodiment

Figure 1:
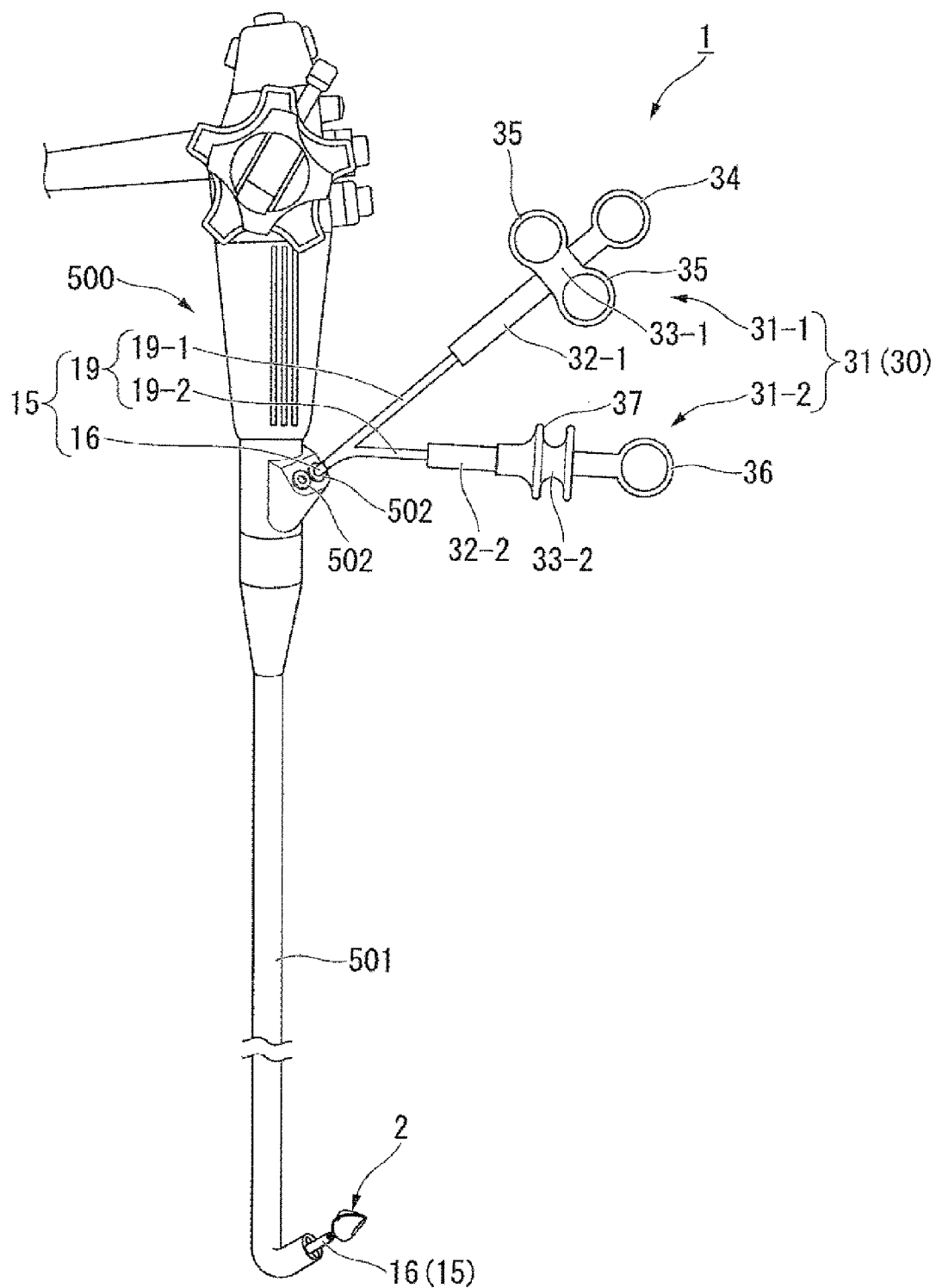
FIG. 1 is an overall view showing a treatment instrument of a first embodiment of the invention, and an endoscope apparatus used with the treatment instrument.

A treatment instrument of a first embodiment of the invention will be described. FIG. 1 is an overall view showing the treatment instrument of the present embodiment, and an endoscope apparatus 500 used with the treatment instrument.

As shown in FIG. 1, the treatment instrument 1 is a treatment instrument used with the endoscope apparatus 500. The configuration of the endoscope apparatus 500 used with the treatment instrument 1 is not particularly limited. For example, in the present embodiment, the endoscope apparatus 500 is a flexible endoscope that includes an elastic insertion section 501 to be inserted into a stomach from a mouth, and has a treatment instrument channel 502 for allowing the treatment instrument 1 to be inserted therethrough provided within the insertion section 501.

Figure 2:
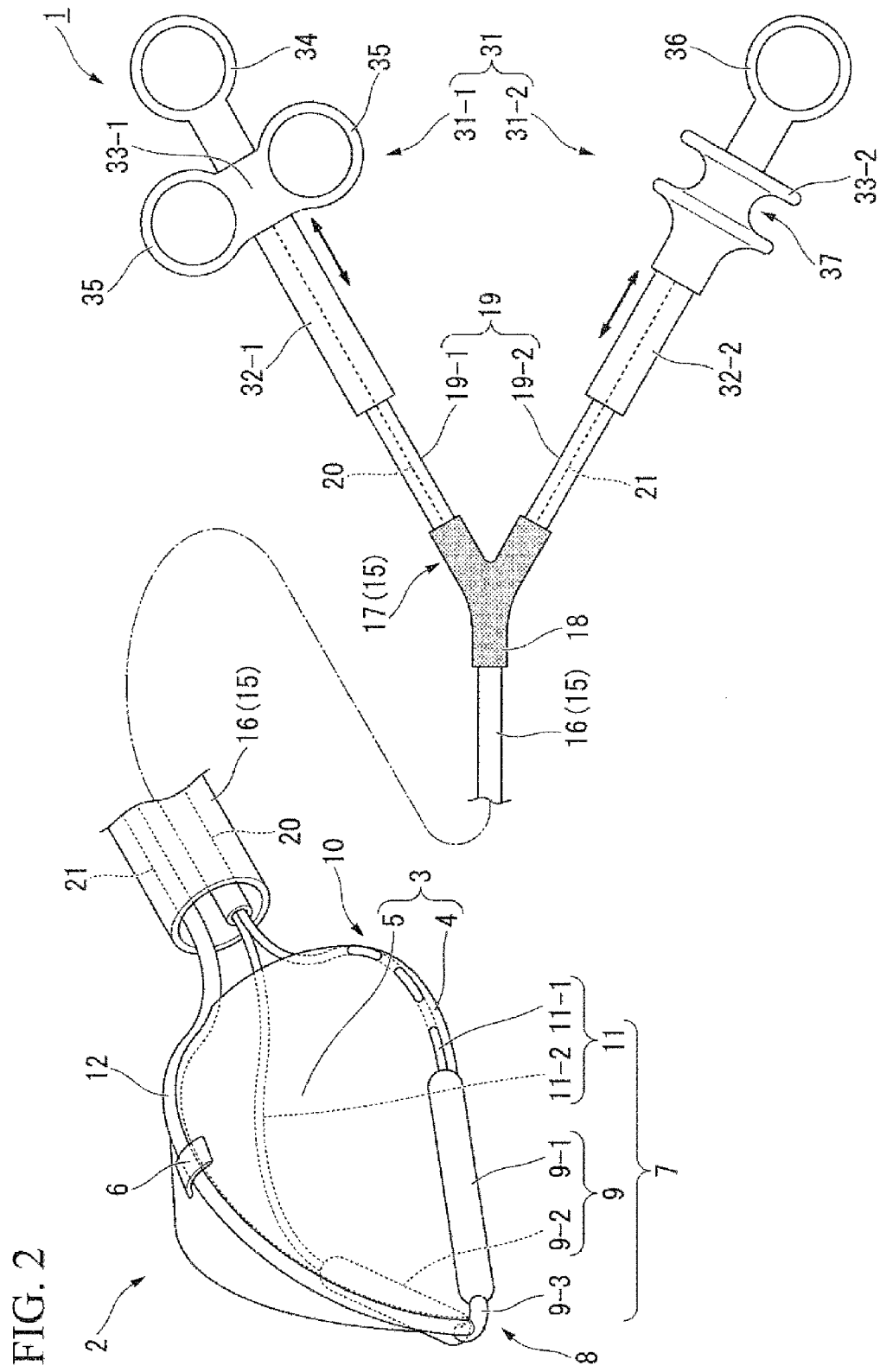
FIG. 2 is a perspective view of the treatment instrument of the first embodiment of the invention.

FIG. 2 is a perspective view of the treatment instrument 1.

As shown in FIG. 2, the treatment instrument 1 includes a treatment section 2 that performs a treatment within a body, an insertion section 15 that has the treatment section 2 at the distal end thereof, and an operation portion 30 (operation means) provided at a proximal end of the insertion section 15. In the present embodiment, the side of the treatment instrument 1 where the treatment section 2 is provided will be described as a distal end side. Additionally, the side of the treatment instrument 1 where the operation portion 30 is provided will be described as a proximal end side. To describe this in detail, the treatment instrument 1 further includes a tubular longitudinal-axis member 16 that is provided to extend along a longitudinal axis; a collecting member 3 that is provided at the distal end of the longitudinal-axis member 16 and has an opening portion 4 for introducing a tissue and a containing portion 5 including an internal space for containing the tissue in communication with the opening portion 4; a frame part 7 that is provided along the edge of the opening portion 4 in order to define the shape of the opening portion 4, has a proximal end portion capable of being housed inside the longitudinal-axis member 16, and operates so that the opening portion 4 is closed if the proximal end portion is housed inside the longitudinal-axis member 16; an opening operating member 20 that is connected to the proximal end portion of the frame part 7 and is provided so as to be movable through the longitudinal-axis member 16 along the longitudinal axis; a volume adjusting member (curved portion) 12 that has a first end portion fixed to a distal end portion of the frame part 7 and a second end portion connected to the first end portion and provided to extend toward the proximal end portion of the frame part 7 and that is formed in a curved shape along the containing portion from the first end portion to the second end portion; and a volume operating member (operating member) 21 that is connected to the second end portion of the volume adjusting member 12.

Additionally, the operation portion 30 allows the opening operating member 20 to move relative to the longitudinal-axis member 16 and the volume operating member 21 so that the proximal end portion of the frame part 7 is pulled into the longitudinal-axis member 16.

As shown in FIG. 2, the treatment section 2 includes the collecting member 3 for collecting tissues, such as a lesion, the frame part 7 that supports the collecting member 3, and the volume adjusting member 12 that deforms the collecting member 3.

The collecting member 3 has the opening portion 4 and the containing portion 5 that communicates with the opening portion 4. The collecting member 3 is formed in a bag shape from a thin film having flexibility. In the collecting member 3, a tissue (including a necrotic tissue) or the like is contained in the containing portion 5 through the opening portion 4. In the present embodiment, the tissue or the like contained in the containing portion 5 are configured so as not to leak out from other than the opening portion 4. Additionally, a tunnel portion 6 is provided at the portion of the external surface of the collecting member 3 that is a deepest portion (for example, a portion that is located at a deepest position from the opening portion 4 in a case where the containing portion 5 is viewed from a side surface) of the containing portion 5. The volume adjusting member 12 to be described below is inserted through the tunnel portion 6. In the present embodiment, the tunnel portion 6 is configured by sticking and fixing the same film-like member as the thin film that constitutes the collecting member 3, to the collecting member 3. Additionally, the tunnel portion 6 has a through hole through which the volume adjusting member 12 can be advanced and retracted.

Figure 3:
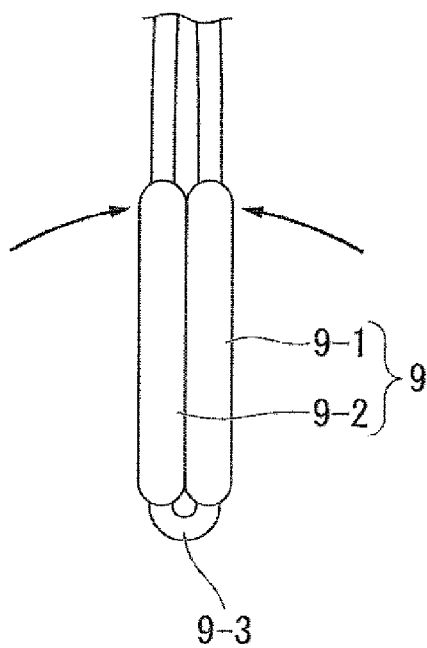
FIG. 3 is a plan view showing the configuration of a portion of a treatment section in the treatment instrument of the first embodiment of the invention.
Figure 4:
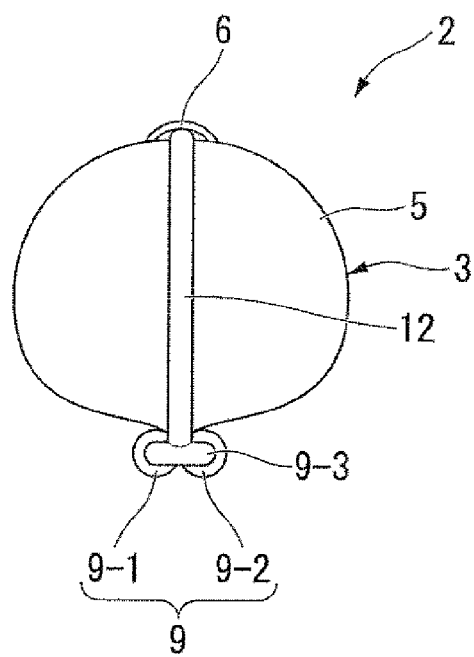
FIG. 4 is a front view showing the configuration of a portion of the treatment section of the first embodiment of the invention.
Figure 5:
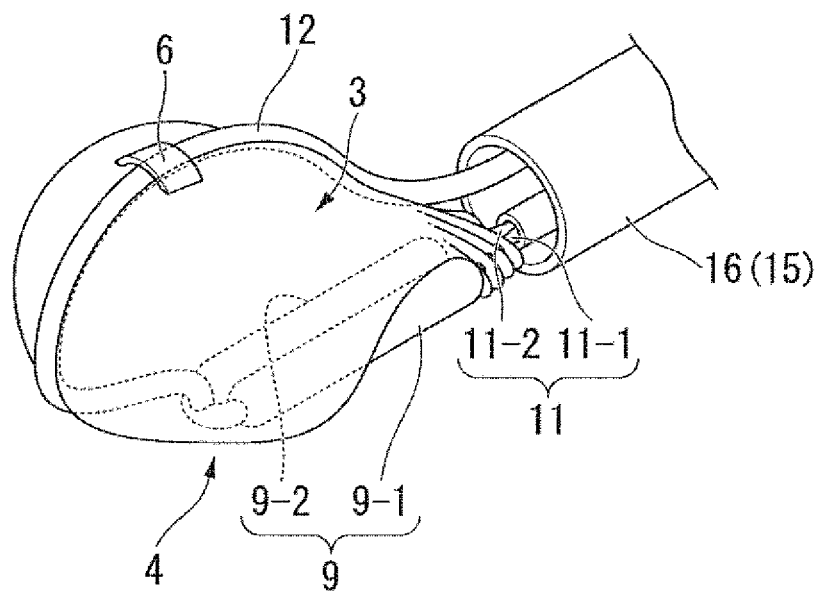
FIG. 5 is a perspective view showing the configuration of a portion when an opening of a collecting member is closed.

FIG. 3 is a front view showing the configuration of a portion of the treatment instrument 1 when the opening portion 4 of the collecting member 3 is closed. FIG. 4 is a plan view showing the configuration of a portion of the treatment instrument 1 in the state where the opening portion 4 of the collecting member 3 is closed. FIG. 5 is a perspective view showing the state where the opening portion 4 of the collecting member 3 is closed.

As shown in FIGS. 2, 3, and 4, the frame part 7 includes an opening closing portion 8 that is fixed to a distal end side of the opening portion 4 of the collecting member 3, and a preceding closing portion 10 that is provided on the proximal end side of the opening closing portion 8.

The opening closing portion 8 includes two rigid portions 9 (a rigid portion 9-1 and a rigid portion 9-2) that are formed in a rod shape and a springy connecting portion 9-3 that connects the distal ends of the respective rigid portions 9 to each other.

The respective rigid portions 9 are formed in a rod shape. As the respective rigid portions 9 are closed so that the respective rigid portions 9 are substantially parallel to each other, the opening portion 4 is closed. In addition, when proximal ends of the respective rigid portions 9 are closed, the collecting member 3 may be pinched between the respective rigid portions 9. A connecting portion between the distal ends of the respective rigid portions 9 has a spring property, and the proximal ends of the respective rigid portions 9 are configured so as to be openable and closable, with the distal ends of the respective rigid portions 9 as turning centers.

The preceding closing portion 10 includes a pair of closing wires 11 (a closing wire 11-1 and a closing wire 11-2) that are connected to the proximal ends of the respective rigid portions 9.

The closing wire 11-1 is fixed to the proximal end of the rigid portion 9-1, and is an elastic wire that has a curved shape when an external force is not applied. The closing wire 11-1 is thrust into the collecting member 3 so as to sew the collecting member 3 along the edge of the opening portion 4 of the collecting member 3.

The closing wire 11-2 is fixed to the proximal end of the rigid portion 9-2, and is an elastic wire that has a curved shape when an external force is not applied. In the present embodiment, the curved shape of the closing wire 11-2 is the same as that of the closing wire 11-1. Additionally, the closing wire 11-1 and the closing wire 11-2 are arranged so as to be symmetrical with respect to a line. The closing wire 11-2 is thrust into the collecting member 3 so as to sew the collecting member 3 along the edge of the opening portion 4 of the collecting member 3. The proximal end of the closing wire 11-2 is fixed to the proximal end of the closing wire 11-1 that makes a pair with the closing wire 11-2. As methods for fixing the proximal end of the closing wire 11-2 and the proximal end of the closing wire 11-1 to each other, well-known fixing methods, such as welding, crimping, brazing, and soldering, can be appropriately adopted. The proximal end of the closing wire 11-2 and the proximal end of the closing wire 11-1 are fixed to a distal end of the opening operating member 20 to be described below, by the above well-known fixing methods.

The distal ends of the respective closing wires 11 bias the respective rigid portions 9 so as to push out the proximal ends of the respective rigid portions 9 when an external force is not applied to the respective closing wires 11. At this time, the opening portion 4 of the collecting member 3 is brought into in an open state by the respective rigid portions 9 and the respective closing wires 11. Additionally, as shown in FIG. 5, if the respective closing wires 11 are elastically deformed so that the distal ends of the respective closing wires 11 approach each other, the proximal ends of the respective rigid portions 9 are moved so as to approach each other, and thereby, the opening portion 4 is brought into a closed state.

In this way, in the present embodiment, the shape of the opening portion 4 of the collecting member 3 is defined by the frame part 7 provided at the edge of the opening portion 4.

As shown in FIG. 2, the volume adjusting member 12 is a linear member that has one end fixed to the connecting portion between the distal ends of the respective rigid portions 9, and is attached to the containing portion 5. The volume adjusting member 12 is configured so as to pass through the deepest portion of the containing portion 5. In the present embodiment, the volume adjusting member 12 is inserted through the tunnel portion 6 of the collecting member 3. A proximal end of the volume adjusting member 12 is inserted into the longitudinal-axis member 16 from the distal end of the longitudinal-axis member 16 to be described below. Additionally, the proximal end of the volume adjusting member 12 is fixed to a distal end of the volume operating member 21 (to be described below) inside the longitudinal-axis member 16.

The volume adjusting member 12 is constituted by an elastic member that has a curved shape along the external surface of the collecting member 3 when the volume of the containing portion 5 of the collecting member 3 is the greatest. Thereby, the volume adjusting member 12 makes a space capable of containing a tissue formed in the containing portion 5 when delivered from the distal end of the longitudinal-axis member 16 to be described below.

As shown in FIG. 2, the insertion section 15 includes the longitudinal-axis member 16 that has a longitudinal axis, and a branch member 17 that is connected to the longitudinal-axis member 16 and the operation portion 30. A distal end of the insertion section 15 is a member to be inserted into the treatment instrument channel 502 of the endoscope apparatus 500, such as a flexible endoscope.

The longitudinal-axis member 16 is a tubular member that opens on a distal end side and a proximal end side. The outline of an inner cavity of the longitudinal-axis member 16 is formed in a circular shape in a cross-section orthogonal to the longitudinal axis. In the present embodiment, the number of through holes that allows the distal end and proximal end of the longitudinal-axis member 16 to communicate with each other is one. Even if the treatment instrument channel 502 of the endoscope apparatus 500 is in a curved state, the longitudinal-axis member 16 has elasticity such that the longitudinal-axis member can be advanced and retracted inside the treatment instrument channel 502.

The branch member 17 is a tubular member. A distal end of the branch member 17 is connected to the proximal end of the longitudinal-axis member 16. Additionally, a proximal end of the branch member 17 is connected to the distal end of the operation portion 30. Although detailed description will be made below, in the present embodiment, the proximal end of the branch member 17 is connected to two operating body portions 31 (an operating body portion 31-1 and an operating body portion 31-2) that are portions of the operation portions 30. The branch member 17 is formed with a main conduit 18 and branch conduits 19 (a branch conduit 19-1 and a branch conduit 19-2). The main conduit 18 communicates with the through hole of the longitudinal-axis member 16. The branch conduits 19 (the branch conduit 19-1 and the branch conduit 19-2) branches from the main conduit 18 in an intermediate portion of the branch member 17 and extend to the two operating body portions 31.

The opening operating member 20 and the volume operating member 21 are inserted through the longitudinal-axis member 16 and the branch member 17. A distal end of the opening operating member 20 is fixed to the proximal ends of the respective closing wires 11. A distal end of the volume operating member 21 is fixed to the proximal end of the volume adjusting member 12. Additionally, the volume operating member 21 is provided so as to be movable along the longitudinal axis with respect to the opening operating member 20.

The opening operating member 20 is a member for transmitting an operating force from the operation portion 30 to the respective closing wires 11. The opening operating member 20 has rigidity such that the respective closing wires 11 can be pulled into the longitudinal-axis member 16 or the respective closing wires 11 can be pushed out of the distal end of the longitudinal-axis member 16. Moreover, the opening operating member 20 is a linear member that has flexibility such that the opening operating member can be curved along the treatment instrument channel 502 (refer to FIG. 1) of the endoscope apparatus 500. The opening operating member 20 is inserted through the branch conduit 19-1 in the branch member 17 and is connected to the operating body portion 31-1.

The volume operating member 21 is a member for transmitting an operating force from the operation portion 30 to the volume adjusting member 12, and is a linear member that has flexibility such that the volume operating member can be curved along the treatment instrument channel 502 of the endoscope apparatus 500. Additionally, the volume operating member 21 has rigidity such that a proximal end side of the volume adjusting member 12 can be pulled into the longitudinal-axis member 16 or the volume adjusting member 12 can be pushed out of the distal end of the longitudinal-axis member 16. The volume operating member 21 is inserted through the branch conduit 19-2 in the branch member 17 and is connected to the operating body portion 31-2.

The operation portion 30 includes the operating body portion 31-1 that is connected to the branch conduit 19-1 and the operating body portion 31-2 that is connected to the branch conduit 19-2.

The operating body portion 31-1 has a shaft portion 32-1 that has a distal end fixed to the branch member 17, and a slider 33-1 that is attached to the shaft portion 32-1.

A proximal end of the shaft portion 32-1 is formed with a ring portion 34 on which an operator can hook his/her finger.

The slider 33-1 has the proximal end of the opening operating member 20 fixed thereto, and is slidingly movable with respect to the shaft portion 32-1. Additionally, the slider 33-1 is formed with a ring portion 35 on which the operator can hook his/her finger.

The operating body portion 31-1 is configured in a shape such that the operator can pass his/her thumb through the ring portion 34 and pass two of the other four fingers through the ring portion 35, thereby conveniently holding the operating body portion 31-1.

The operating body portion 31-2 has a shaft portion 32-2 that has a distal end fixed to the branch member 17, and a slider 33-2 that is attached to the shaft portion 32-2.

A proximal end of the shaft portion 32-2 is formed with a ring portion 36 on which the operator can hook his/her finger.

The slider 33-2 has the proximal end of the volume operating member 21 fixed thereto, and is slidingly movable with respect to the shaft portion 32-2. Additionally, the slider 33-2 is a member that is formed in a substantially tubular shape that has a recessed portion 37, on which the operator hook his/her finger, at an intermediate portion thereof.

The operating body portion 31-2 is configured in a shape such that the operator can pass his/her thumb through the ring portion 36 and pinch the recessed portion 37 with the other fingers, thereby conveniently holding the operating body portion 31-2.

The operating body portion 31-1 and the operating body portion 31-2 have mutually different shapes or sizes. Thereby, distinction between the operating body portion 31-1 that operates the opening operating member 20 and the operating body portion 31-2 that operates the volume operating member 21 becomes easy, and an erroneous operation can be reduced. In addition, the operating body portion 31-1 and the operating body portion 31-2 may have the same shape or the same size.

Figure 6:
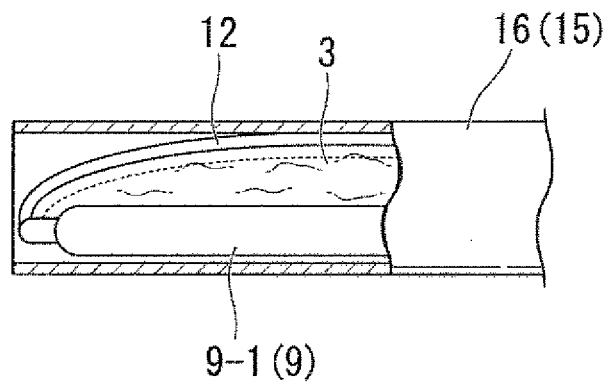
FIG. 6 is a partial cross-sectional view showing the state of the treatment section before the start of a procedure using the treatment instrument of the first embodiment of the invention.
Figure 7:
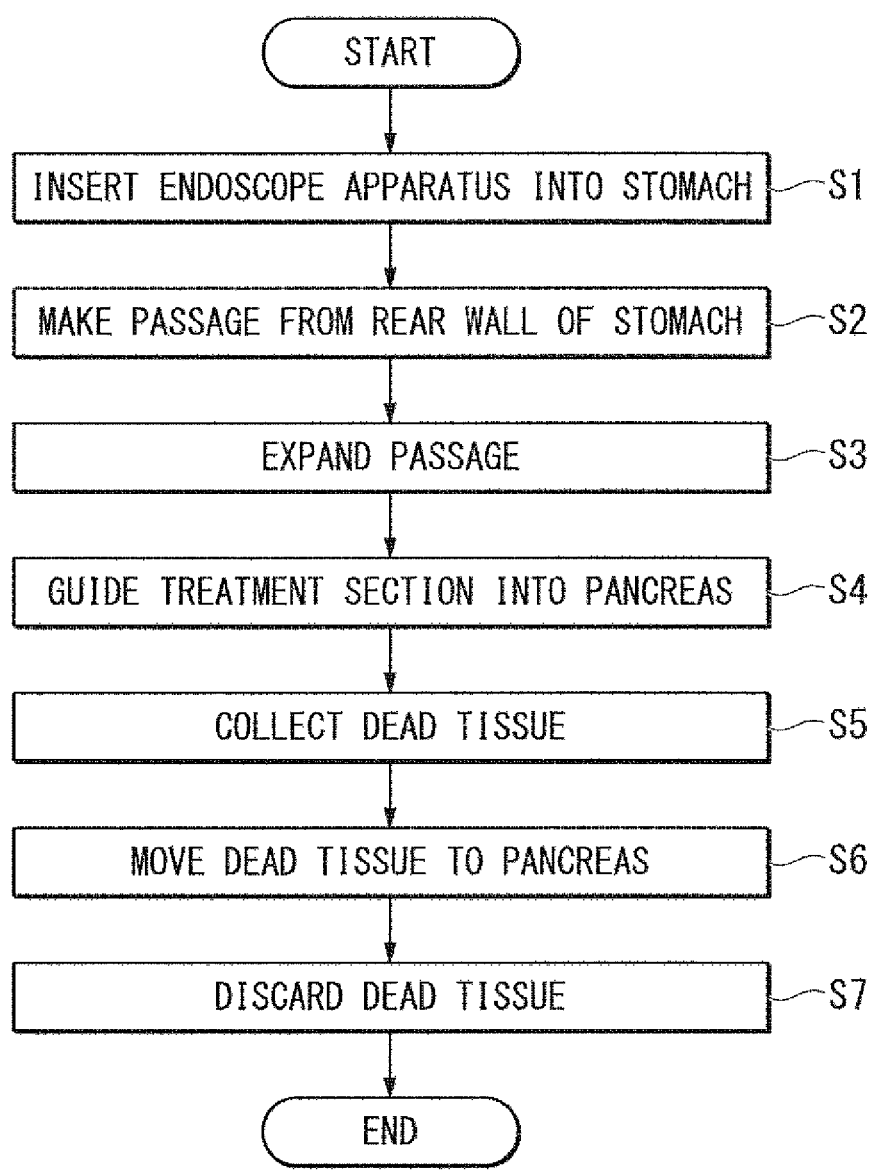
FIG. 7 is a flowchart showing the flow of an example of the procedure using the treatment instrument of the first embodiment of the invention.

The operation of the treatment instrument 1 of the present embodiment will be described taking an example of a procedure using the treatment instrument 1. FIG. 6 is a partial cross-sectional view showing the state of the treatment section before the start of the procedure using the treatment instrument. FIG. 7 is a flowchart showing the flow of the procedure using the treatment instrument. FIGS. 8 to 14 are explanatory views showing one process of the procedure.

The procedure illustrated in the present embodiment is a procedure called pancreatic necrosectomy. The pancreatic necrosectomy is a procedure that rakes out the tissue of the pancreas necrosed within the pancreas to the inside of the alimentary canal or the outside of the body to thereby remove the tissue.

In order to perform this procedure, the endoscope apparatus 500, a puncture needle 510 for an endoscope, a dilation catheter 520 for an endoscope, and the treatment instrument 1 of the present embodiment are used.

Additionally, as shown in FIG. 6, before the start of the procedure, the treatment instrument 1 of the present embodiment is set in a form such that the treatment section 2 is housed inside the longitudinal-axis member 16. That is, before the start of the procedure, the slider 33-1 shown in FIG. 2 is brought into a state where the slider is pulled to a proximal end side of the shaft portion 32-1, and the slider 33-2 is brought into a state where the slider is pulled to a proximal end side of the shaft portion 32-2. Thereby, as shown in FIG. 6, the collecting member 3 is brought into a state where the collecting member is housed inside the longitudinal-axis member 16.

FIG. 7 is a flowchart showing the flow of this procedure.

First, the insertion section 501 of the endoscope apparatus 500 is inserted into a patient's stomach (Step S1 shown in FIG. 7).

Figure 8:
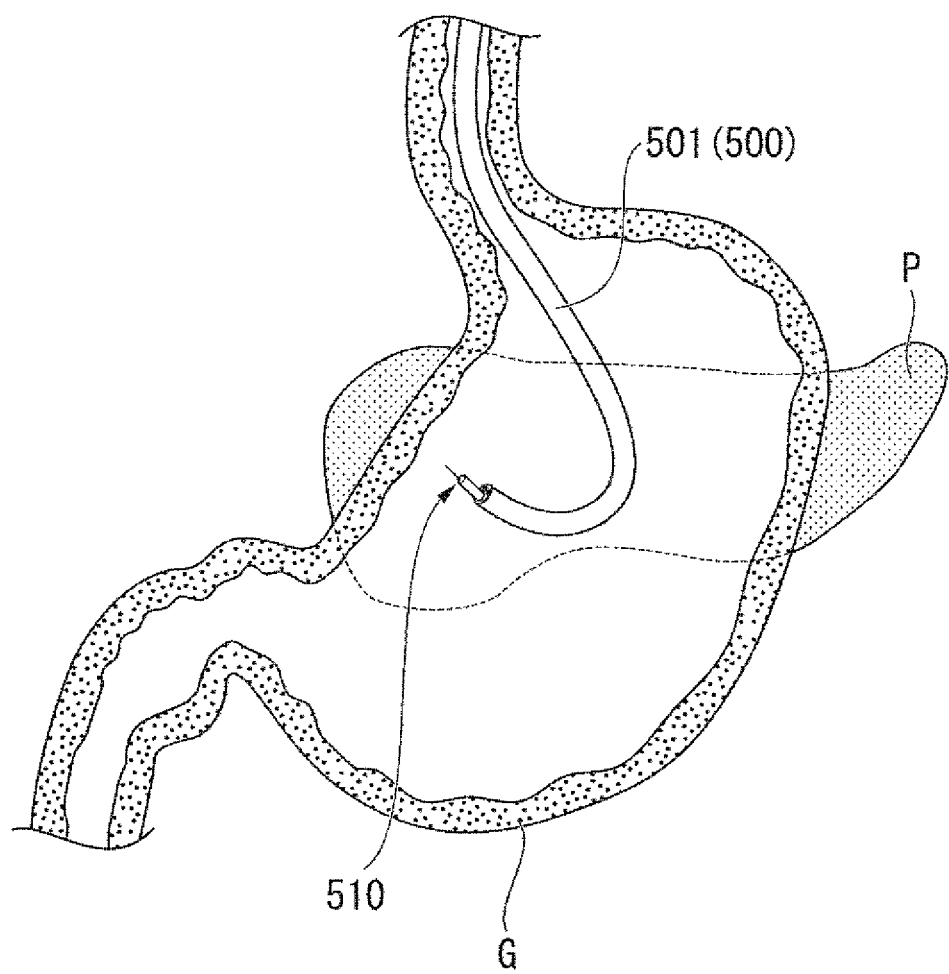
FIG. 8 is an explanatory view showing one process of the procedure.
Figure 9:
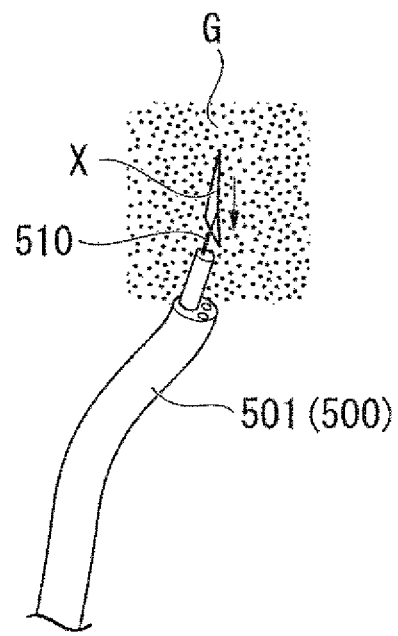
FIG. 9 is an explanatory view showing one process of the procedure.

In Step S1, as shown in FIG. 8, the distal end of the insertion section 501 of the endoscope apparatus 500 is arranged within a stomach G through an esophagus from a mouth. In this procedure, as the operator observes the inside of the stomach using an endoscope image, a site suitable for incision is selected.

Step S1 is ended by this, and the procedure proceeds to Step S2.

Step S2 is a step of incising the rear wall of the stomach to form passages for guiding the treatment instrument 1 into the pancreas, in the stomach and the pancreas.

In Step S2, the above-described puncture needle 510 for an endoscope is attached to the treatment instrument channel 502 of the endoscope apparatus 500 for the purpose of incising the site selected in the above Step S1. The operator makes a hole in the rear wall of the stomach using the puncture needle 510 for an endoscope, and forms this hole as an opening portion X (refer to FIG. 9).

Step S2 is ended by this, and the procedure proceeds to Step S3.

Step S3 is a step of expanding the passages (opening portions X) formed in the above Step S2.

In Step S3, a guide wire is introduced into the inside of the body through an internal cylinder (not shown) provided in the puncture needle 510 for an endoscope. Moreover, the dilation catheter 520 for an endoscope is introduced into the inside of the body along with the guide wire. A distal end of the guide catheter for an endoscope is guided to the opening portion X formed in the stomach by the guide wire.

Figure 10:
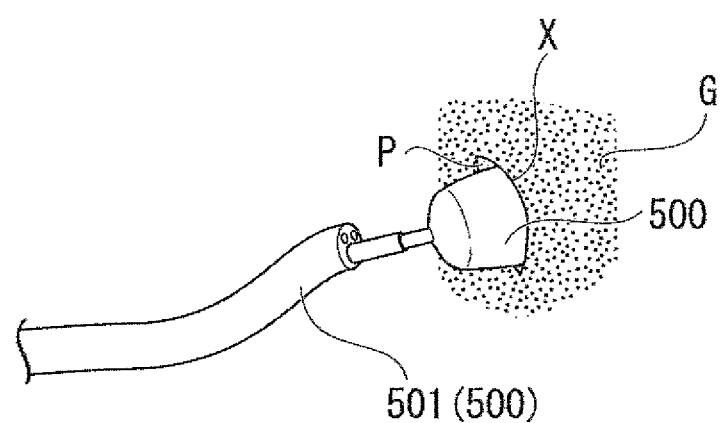
FIG. 10 is an explanatory view showing one process of the procedure.
Figure 11:
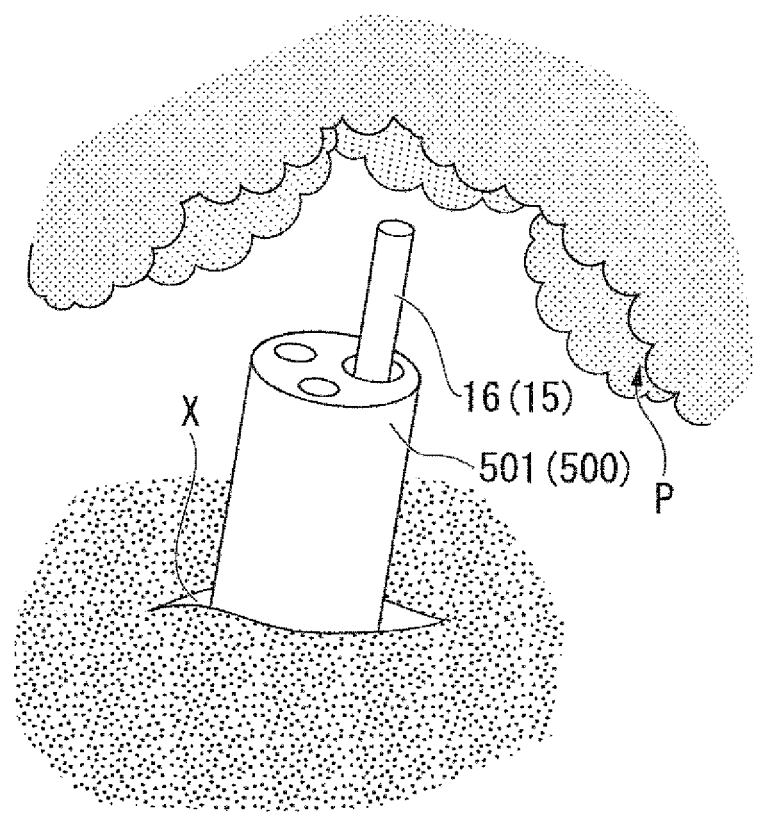
FIG. 11 is an explanatory view showing one process of the procedure.
Figure 12:
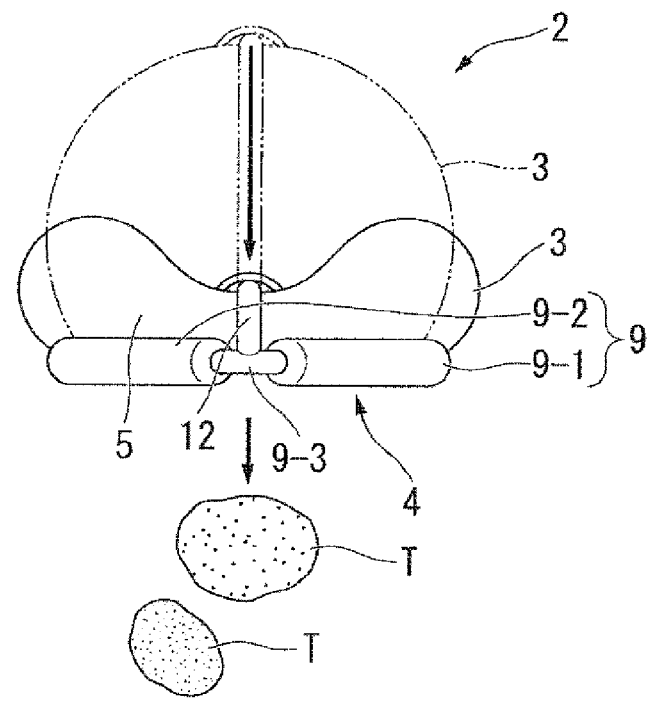
FIG. 12 is an explanatory view showing one process of the procedure.

If the dilation catheter 520 for an endoscope is guided to the opening portions X, a balloon portion of the dilation catheter 520 for an endoscope is inserted into the opening portions X formed in the above Step S2. Thereafter, the balloon portion is expanded, as shown in FIG. 10, such that the opening portions X are pushed out to a desired size. Thereby, in Step S3, the passages that are expanded to a size such that the treatment section 2 can be inserted into the pancreas from the inside of the stomach are formed in the stomach and the pancreas.

In a case where the opening portions X are further expanded, for example, a high-frequency treatment instrument that incises a tissue using a high-frequency current is used.

If the opening portions X with a desired size are formed, the dilation catheter 520 for an endoscope is removed.

Step S3 is ended by this, and the procedure proceeds to Step S4.

Step S4 is a step of guiding the treatment section 2 into the pancreas through the passages expanded in the above Step S3.

In Step S4, the treatment instrument 1 is attached to the treatment instrument channel 502 of the endoscope apparatus 500 (refer to FIG. 1). Additionally, the puncture needle for an endoscope or the dilation catheter for an endoscope may be detached from the treatment instrument channel, or the treatment instrument 1 may be attached to the treatment instrument channel using the empty guide wire.

The treatment section 2 and the insertion section 15 are inserted into the treatment instrument channel 502. Then, the distal end of the longitudinal-axis member 16 of the treatment instrument 1 protrudes from the distal end of the treatment instrument channel 502. Thereafter, the operator who operates the endoscope apparatus 500 to which the treatment instrument 1 is attached operates to curve or move the insertion section 501 of the endoscope apparatus 500, thereby guiding the distal end of the longitudinal-axis member 16 into the pancreas through the opening portions X formed in the stomach and the pancreas (refer to FIG. 11). If the treatment instrument 1 enters the pancreas, the guide wire is removed.

Step S4 is ended by this, and the procedure proceeds to Step S5.

Step S5 is a step of collecting a necrotic tissue using the treatment section 2 guided into the pancreas in the above Step S4.

In Step S5, the slider 33-1 is moved to the distal end side of the shaft portion 32-1, and the opening operating member 20 is moved to the distal end side of the longitudinal-axis member 16. Thereby, the treatment section 2 fixed to the distal end of the opening operating member 20 is pushed out of the distal end of the longitudinal-axis member 16. At this time, the volume adjusting member 12 and the volume operating member 21 are also moved to the distal end side, and the slider 33-2 is moved to the distal end side of the shaft portion 32-2 in the operating body portion 31-2.

If the treatment section 2 is pushed out of the distal end of the longitudinal-axis member 16, the respective closing wires 11 are restored to a curved state, and the respective rigid portions 9 are moved so that the proximal ends of the respective rigid portions 9 are spaced apart from each other. Thereby, the opening portion 4 of the collecting member 3 is brought into an open state (refer to FIG. 2). At this time, the tunnel portion 6 of the collecting member 3 is located near the opening surface of the opening portion 4, and the volume of the collecting member 3 is formed so as to be the minimum. In addition, the operation of unwinding the treatment section 2 from the distal end of the longitudinal-axis member 16 may be performed in the above Step S4.

Next, the operator adjusts the position of the treatment section 2 using an image that can be seen via the endoscope apparatus 500 so that necrotic tissue serving as a collection target is located in the opening portion 4 of the collecting member 3.

If the necrotic tissue serving as a collection target is arranged within the opening portion 4 of the collecting member 3, as shown in FIG. 2, the operator further moves the slider 33-2 to the distal end side of the shaft portion 32-2 when the position of the slider 33-1 is fixed to the shaft portion 32-1. Then, the volume operating member 21 that has the proximal end fixed to the slider 33-2 moves to the distal end side of the longitudinal-axis member 16 along the longitudinal axis. Moreover, the volume adjusting member 12 fixed to the distal end of the volume operating member 21 is restored to its original curved state, and pulls the deepest portion of the collecting member 3 in the tunnel portion 6 to increase the volume of the containing portion 5. Thereby, the opening portion 4 opens, and the volume of the containing portion 5 becomes large while a predetermined opening area is maintained.

As the opening operating member 20 and the volume operating member 21 are operated in this way, respectively, the collecting member 3 housed inside the longitudinal-axis member 16 expands in a bag shape outside the longitudinal-axis member 16 (refer to FIG. 2). The operator operates to curve or move the insertion section 501 of the endoscope apparatus 500 or advances and retracts the longitudinal-axis member 16 of the treatment instrument 1 with respect to the treatment instrument channel 502, thereby moving the treatment section 2 within the pancreas. Thereby, a necrotic tissue can be raked out using the frame part 7, especially the respective rigid portions 9. Additionally, by moving the slider 33-1 to the proximal end side of the shaft portion 32-1 so that the respective closing wires 11 are pulled into the longitudinal-axis member 16, thereby closing the respective rigid portions 9, the necrotic tissue located between the respective rigid portions 9 can be cut. The necrotic tissue that is raked out or cut is contained inside the collecting member 3.

Step S5 is ended by this, and the procedure proceeds to Step S6.

Step S6 is a step of moving the necrotic tissue collected in the above Step S5 out of the pancreas.

In Step S6, the operator moves the slider 33-1 to the proximal end side of the shaft portion 32-1 when the position of the slider 33-2 with respect to the shaft portion 32-2 is fixed. Then, the opening operating member 20 that has the proximal end fixed to the slider 33-1 moves to the proximal end side of the longitudinal-axis member 16 along the longitudinal axis of the longitudinal-axis member 16. Moreover, the respective closing wires 11 fixed to the distal end of the opening operating member 20 are pulled into the longitudinal-axis member 16 from the distal end of the longitudinal-axis member 16. At this time, since the respective closing wires 11 are pulled into the longitudinal-axis member 16 when the proximal end of the collecting member 3 is supported by the distal end of the longitudinal-axis member 16, the proximal end side of the opening portion 4 of the collecting member 3 is closed.

If the respective closing wires 11 are pulled into the longitudinal-axis member 16, the respective closing wires 11 become parallel to the longitudinal axis of the longitudinal-axis member 16, and the distal ends of the respective closing wires 11 are brought into a proximity state. At this time, the respective rigid portions 9 that have the proximal ends fixed to the distal ends of the respective closing wires 11 are brought into a state where the rigid portion 9-1 and the rigid portion 9-2 are parallel to each other and the outer peripheral surface of the rigid portion 9-1 and the outer peripheral surface of the rigid portion 9-2 touch each other. That is, the distal end side of the opening portion 4 of the collecting member 3 is closed by the rigid portion 9-1 and the rigid portion 9-2.

As the respective closing wires 11 are pulled into the longitudinal-axis member 16 in this way, both the proximal end side and distal end side of the opening portion 4 are closed and the whole opening portion 4 is brought into a closed state (refer to FIGS. 4 and 5).

In the process during which the respective closing wires 11 are pulled into the longitudinal-axis member 16, the volume operating member 21 is not moved with respect to the longitudinal-axis member 16. Accordingly; the proximal end of the volume adjusting member 12 is moved neither to the distal end side nor to the proximal end side. For this reason, the volume adjusting member 12 is maintained in a curved state, and the depth dimension of the containing portion 5 of the collecting member 3 hardly changes before and after the opening portion 4 is closed. That is, even if the opening portion 4 of the collecting member 3 is closed, a sufficient space that contains the necrotic tissue is secured in the containing portion 5.

The operator pulls back the treatment section 2 into the stomach from the inside of the pancreas by moving the insertion section 501 of the endoscope apparatus 500 or moving the longitudinal-axis member 16 with respect to the treatment instrument channel 502, when the opening portion 4 of the collecting member 3 is closed. When a large amount of necrotic tissue is contained inside the collecting member 3, the collecting member 3 may be fastened by the inner surface of the passage formed in the inner wall of the stomach. However, in the treatment instrument 1 of the present embodiment, the opening portion 4 that is a main opening of the collecting member 3 is closed. Therefore, the necrotic tissue does not easily leak out of the collecting member 3. For this reason, the necrotic tissue can be efficiently moved into the stomach from the inside of the pancreas.

Step S6 is ended by this, and the procedure proceeds to Step S7.

Step S7 is a step of discarding the necrotic tissue into the stomach.

In Step S7, first, the operator moves the slider 33-1 to the distal end side of the shaft portion 32-1, and moves the opening operating member 20 to the distal end side of the longitudinal-axis member 16. Thereby, the respective closing wires 11 housed inside the longitudinal-axis member 16 are pushed out of the distal end of the longitudinal-axis member 16. Then, the frame part 7 expands the opening portion 4 by the restoring forces of the respective closing wires 11.

Next, the operator moves the slider 33-2 to the proximal end side of the shaft portion 32-2 when the position of the slider 33-1 with respect to the shaft portion 32-1 is fixed. Then, the volume operating member 21 that has the proximal end fixed to the slider 33-2 moves to the proximal end side of the longitudinal-axis member 16 along the longitudinal axis. Moreover, the volume adjusting member 12 fixed to the distal end of the volume operating member 21 is also moved to the proximal end side. Thereby, the collecting member 3 coupled to the volume adjusting member 12 in the tunnel portion 6 is deformed so that the tunnel portion 6 approaches the opening surface. That is, the volume of the containing portion 5 becomes small when the opening portion 4 opens. Thereby, the necrotic tissue T can be pushed out of the collecting member 3 from the opening portion 4 while maintaining a state where the opening portion 4 opens (refer to FIG. 12).

The necrotic tissue pushed out of the opening portion 4 of the collecting member 3 is discarded into the stomach. The necrotic tissue T discarded into the stomach is excreted through the alimentary canal.

Additionally, in Step S7, the treatment section 2 in which the necrotic tissue is contained may be taken out to the outside of the body if needed. In this case, the whole treatment instrument 1 may be taken out to the outside of the body together with the endoscope apparatus 500. As long as the collecting member 3 has a size capable of being pulled into the treatment instrument channel 502 when the necrotic tissue is contained in the collecting member 3, the collecting member 3 in which the necrotic tissue is contained may be pulled out to the outside of the body through the treatment instrument channel 502. The necrotic tissue taken out to the outside of the body can be used for a pathological examination or the like.

Step S7 is ended by this.

In this procedure, in a case where the amount of a necrotic tissue that is required to be raked out of the pancreas is larger than the maximum volume of the collecting member 3, the steps from the above Step S4 to the above Step S7 can also be repeated muldistal endle times.

In the related art, cup-type forceps, basket-type forceps, or the like are used as a treatment instrument to be used to perform necrosectomy. In the cup-type forceps or basket-type forceps that have been used in the related art, the size of the treatment instrument is restricted to a size capable of being inserted through the treatment instrument channel 502 of the flexible endoscope. For this reason, in the above cup-type forceps or basket-type forceps, the size of a cup or a basket should have much smaller volume than a volume capable of raking out all necrotic tissues at one time. As a result, since the number of repetitions of steps between collection of a necrotic tissue and discard of the necrotic tissue is increased, there is a problem in that substantial time is required for treatment.

In contrast, the treatment instrument 1 of the present embodiment has the collecting member 3 that can be inserted through the treatment instrument channel 502 when housed inside the longitudinal-axis member 16 and that expands in a bag shape during a treatment. Therefore, a large space for containing a necrotic tissue or the like as compared to the above cup-type forceps or basket-type forceps of the related art can be secured within the collecting member 3. Thereby, in comparison with the cup-type forceps or basket-type forceps of the related art, a tissue can be collected more efficiently under the limitation of dimensions capable of being inserted through the treatment instrument channel 502.

Additionally, the operation portion 30 operates to advance and retract the opening operating member 20 and the volume operating member 21 independently from each other in the direction of the longitudinal-axis of the longitudinal-axis member 16. Thereby, the depth dimension of the containing portion 5 when being measured in the direction intersecting the opening surface defined by the edge of the opening portion 4, and the opening area of the opening portion 4 are adjusted independently from each other. As a result, a tissue can be easily collected even in a place where a space for expanding the containing portion 5 in order to collect the tissue is insufficient.

Additionally, since the respective rigid portions 9 are constituted by rod-shaped members, the shape of the opening portion 4 can be maintained against the elasticity of a necrotic tissue. For this reason, a necrotic tissue is easily collected within the containing portion 5. Additionally a necrotic tissue can be excised while being pinched by the respective rigid portions 9.

Additionally, since the opening portion 4 of the collecting member 3 can be opened and closed as the opening operating member 20 is operated, the tissue within the containing portion 5 does not easily leak out when the opening portion 4 is closed.

Additionally, since the volume of the containing portion 5 of the collecting member 3 varies as the volume operating member 21 is operated, the volume of the containing portion 5 can be reduced when the opening portion 4 opens, and the tissue inside the containing portion 5 can be pushed out of the opening portion 4. Thereby, a tissue can be taken out more easily than by shaking the collecting member 3 or tilting the collecting member 3 to take out a tissue from the opening portion 4.

In addition, the collecting member 3 may have a net-like structure. The collecting member 3 having the net-like structure is formed with meshes as a threadlike member having flexibility is knitted, and has the opening portion 4 and the containing portion 5. The frame part 7 is inserted through meshes so as to sew the meshes along the edge of the opening portion 4 of the collecting member 3. In addition, it is preferable that the size of the meshes formed in the collecting member 3 be appropriately set according to the state of a treatment target. Even in such a configuration, the same effects as the above-described effects are exhibited. Additionally, since the meshes of the collecting member 3 are configured so that a body fluid or the like pass therethrough, the body fluid can be separated from a tissue and solid matter can be collected. For this reason, the proportion of the solid matter that can be contained at one time within the containing portion 5 can be made high, and the number of times of raking out a tissue from the treatment target can be reduced. As a result, the time required for treatment can be shortened.

Additionally, the opening operating member 20 and the respective closing wires 11 may be made of the same member. That is, the proximal ends of the respective closing wires 11 extend to the operation portion 30, and the proximal ends of the respective closing wires 11 are connected to the operating body portion 31-1. In this case, the operating body portion 31-1 can operate to advance and retract the respective closing wires 11 simultaneously to thereby open and close the respective rigid portions 9, similar to the above-described first embodiment. Even in such a configuration, the same effects as the above-described effects are exhibited. Additionally, since the opening operating member 20 and the respective closing wires 11 are made of the same member, as compared to a case where the opening operating member 20 and the respective closing wires 11 are made by connecting separate members, the mechanical strength of a boundary portion between the opening operating member 20 and the respective closing wires 11 is high.

Additionally, the volume adjusting member 12 and the volume operating member 21 may be made of the same member. Even in this case, the same effects as the above-described effects are exhibited. Additionally, since the volume adjusting member 12 and the volume operating member 21 are made of the same member, as compared to a case where the volume adjusting member 12 and the volume operating member 21 are made by connecting separate members, the mechanical strength of a boundary portion between the volume adjusting member 12 and the volume operating member 21 is high. Additionally, the volume adjusting member 12 and the volume operating member 21 may be made of a continuous pliable threadlike member. In this case, if a tissue enters the containing portion 5 through the opening portion 4, the containing portion 5 swells and the volume operating member 21 is pulled to the distal end side. Additionally, if an operator pulls the threadlike volume operating member 21 to the proximal end side, the containing portion 5 contracts and a tissue is pushed out of the collecting member 3 through the opening portion 4. That is, if it is not necessary to move the volume operating member 21 to the distal end side so as to increase the volume of the containing portion 5, the volume operating member 21 does not need to have rigidity capable of resisting the compression in the direction of the central axis. Accordingly, in such a case, a member having a smaller diameter than the above-described volume operating member 21 can be adopted as the volume operating member 21. This can reduce the diameter of the insertion section 15.

Second Embodiment

Next, a treatment instrument of a second embodiment of the invention will be described. In addition, in respective embodiments to be described below; the same constituent elements as those of the above-described first embodiment will be designated by the same reference numerals, and duplicate description will be omitted.

Figure 13:
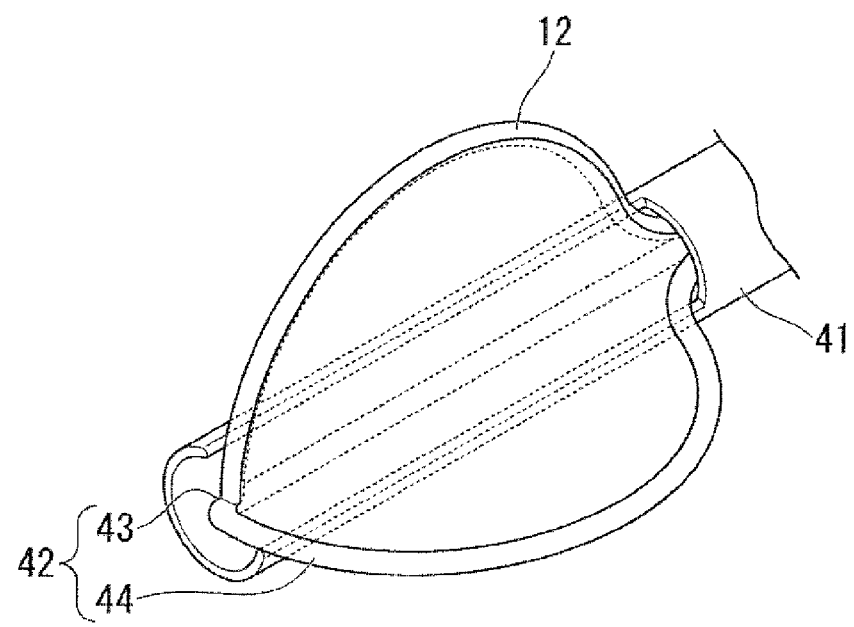
FIG. 13 is a perspective view showing a treatment instrument of a second embodiment of the invention.
Figure 14:
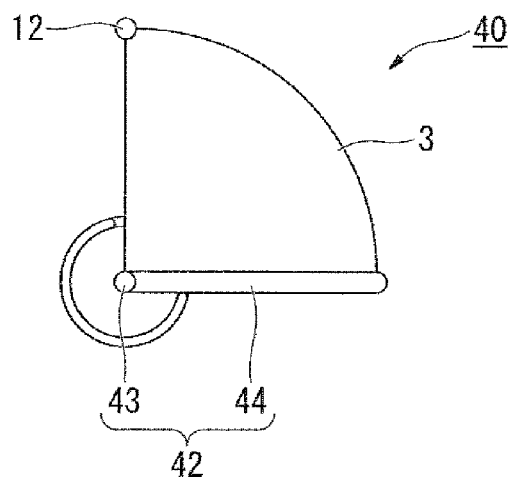
FIG. 14 is a front view showing the treatment instrument of the second embodiment of the invention.
Figure 15:
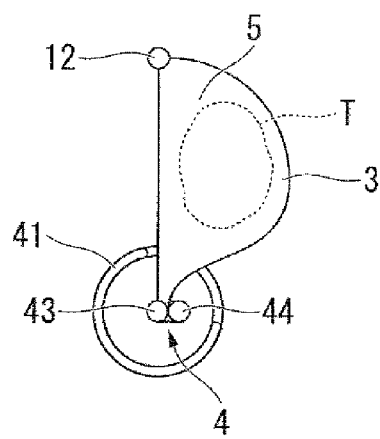
FIG. 15 is a front view showing the treatment instrument of the second embodiment of the invention.
Figure 16:
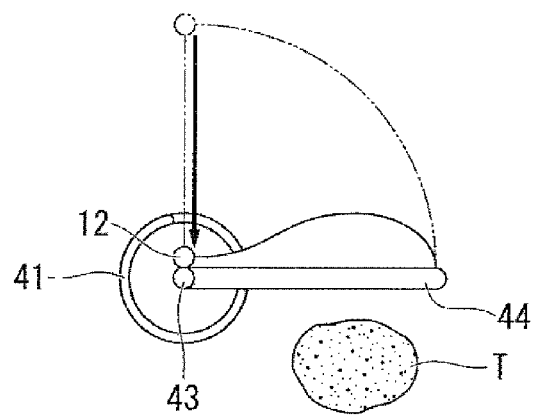
FIG. 16 is a front view showing the treatment instrument of the second embodiment of the invention.

FIG. 13 is a perspective view showing the configuration of a portion of the treatment instrument of the present embodiment. FIG. 14 is a front view showing the configuration of a portion of the treatment instrument of the present embodiment. FIGS. 15 and 16 are views for describing the operation of the treatment instrument of the present embodiment.

As shown in FIGS. 13 and 14, the treatment instrument 40 includes a longitudinal-axis member 41 that has a slit formed in a side wall of a distal end thereof, instead of the longitudinal-axis member 16 described in the first embodiment. Additionally, the treatment instrument 40 includes a closing wire 42 that is formed in a substantially annular shape from a wire having elasticity, instead of the frame part 7 described in the first embodiment. For this reason, the treatment instrument 40 does not include the rigid portions 9.

In the present embodiment, the closing wire 42 has a linear portion 43 that extends in the direction of the central axis of the longitudinal-axis member 41, and an opening forming portion 44 that has the a curved shape that has swelled in the radial direction of the longitudinal-axis member 41.

A distal end of the linear portion 43 and a distal end of the opening forming portion 44 are fixed to each other. Additionally, the linear portion 43 is fixed to the longitudinal-axis member 41 inside the longitudinal-axis member 16. Moreover, the proximal end of the opening forming portion 44 is fixed to the distal end of the opening operating member 20.

The linear portion 43 and the opening forming portion 44 are attached to the collecting member 3 along the edge of the opening portion 4 of the collecting member 3.

In the present embodiment, the treatment instrument 40 does not include the rigid portions 9 described in the first embodiment, and a distal end portion of the longitudinal-axis member 41 and the opening forming portion 44 are configured so as to function as the above rigid portions 9. That is, if the slider 33-1 is moved to the proximal end side of the shaft portion 32-1, the opening forming portion 44 that has a curved shape is pulled into the longitudinal-axis member 41 from the slit of the longitudinal-axis member 41, and is deformed in a linear shape that extends in the direction of the central axis of the longitudinal-axis member 41 (refer to FIG. 15). Thereby, the opening portion 4 of the collecting member 3 is closed. Additionally, the necrotic tissue T can also be excised by pinching the necrotic tissue T by the distal end portion of the longitudinal-axis member 41 and the opening forming portion 44.

As shown in FIG. 16, even in the treatment instrument 40 of the present embodiment, the volume of the containing portion 5 can be made small by the volume adjusting member 12 to discharge the necrotic tissue T from the containing portion 5, similar to the treatment instrument 1 of the above-described first embodiment.

Additionally, in the present embodiment, the opening forming portion 44 has the a curved shape that has swelled in the radial direction of the longitudinal-axis member 41, and the proximal end of the opening forming portion 44 can be advanced and retracted when the linear portion 43 is fixed to the longitudinal-axis member 41. Thereby, if the opening operating member 20 is moved to the distal end side within the longitudinal-axis member 41, the opening forming portion 44 swells toward one direction that is a radial outward side of the longitudinal-axis member 41. In the present embodiment, since the longitudinal-axis member 41 extends to the distal end of the treatment section 2, the strength of the whole treatment section 2 increases, and the treatment section 2 is easily pressed against a tissue.

Third Embodiment

Figure 17:
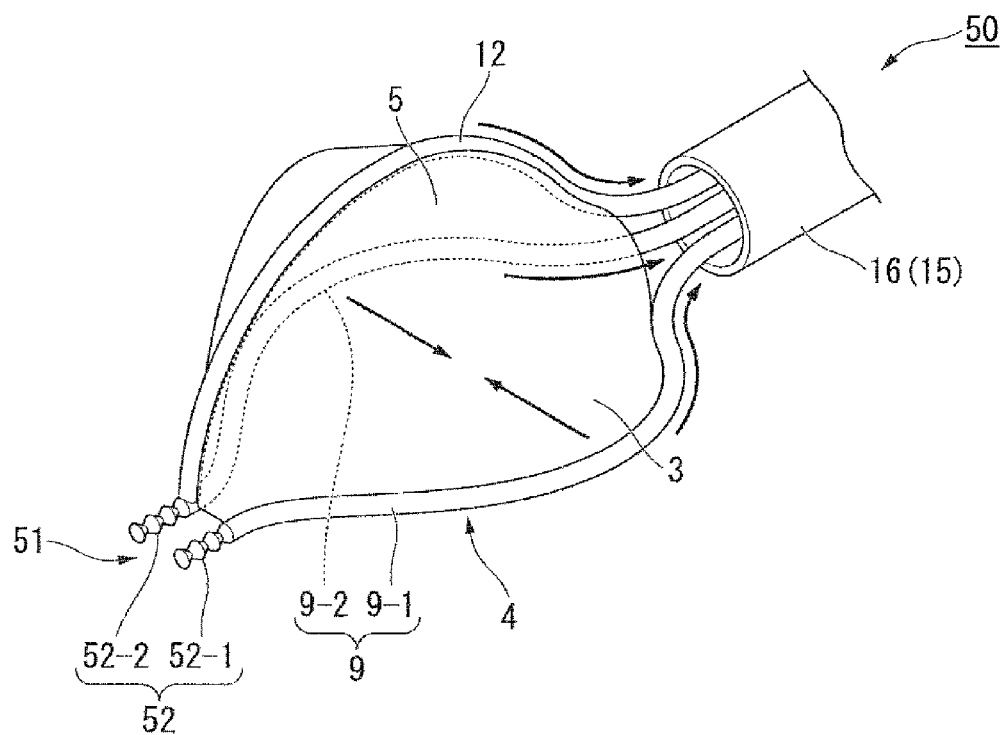
FIG. 17 is a perspective view showing a treatment instrument of a third embodiment of the invention.
Figure 18:
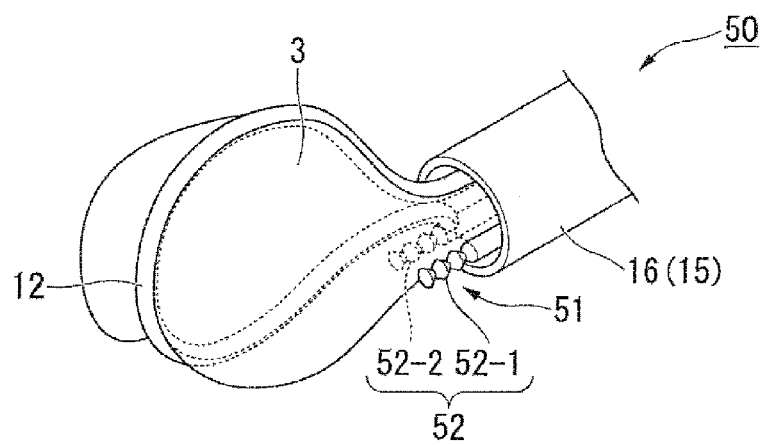
FIG. 18 is a perspective view showing the treatment instrument of the third embodiment of the invention.
Figure 19:
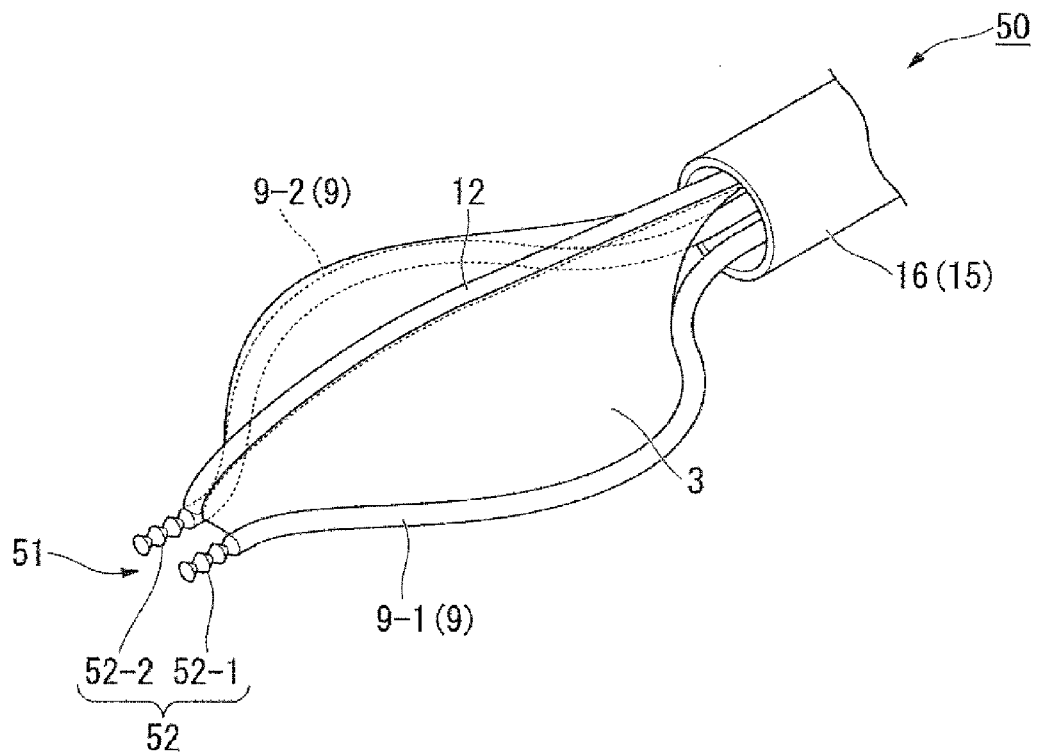
FIG. 19 is a perspective view showing the treatment instrument of the third embodiment of the invention.

Next, a treatment instrument of a third embodiment of the invention will be described. FIG. 17 is a perspective view showing the configuration of a portion of the treatment instrument of the present embodiment. FIGS. 18 and 19 are views for describing the operation of the treatment instrument of the present embodiment.

As shown in FIG. 17, in the treatment instrument 50, the distal ends of the respective rigid portions 9 are not connected to each other. In the treatment instrument 50, a grip forceps portion 51 that grips a tissue is provided at the distal ends of the respective rigid portions 9.

The grip forceps portion 51 has a pair of forceps members 52 (a forceps member 52-1 and a forceps member 52-2) in which antislip irregularities are formed on surfaces that face each other.

In the present embodiment, the distal end of the volume adjusting member 12 is fixed to the opening of the collecting member 3. In addition, the volume adjusting member 12 may be fixed to any one of the distal ends of the respective rigid portions 9.

As shown in FIGS. 18 and 19, in the present embodiment, the pair of forceps members 52 can be closed by pulling the respective closing wires 11 into the longitudinal-axis member 16 so that a tissue or the like can be gripped. If the closing wires 11 are further pulled into the longitudinal-axis member 16 from a state where the pair of forceps members 52 are closed, the opening portion 4 of the collecting member 3 is closed, similar to the above first embodiment.

When the treatment instrument 50 is used, a necrotic tissue can be gripped using the grip forceps portion 51 or a necrotic tissue can be broken by any one or both of the pair of forceps members 52.

The treatment instrument 50 of the present embodiment also exhibits the same effects as the second embodiment, similar to the above first embodiment.

Moreover, according to the treatment instrument 50 of the present embodiment, in a case where there is no gap for arranging the collecting member 3 or the like, the grip forceps portion 51 can be used to move a necrotic tissue or the like to a large place, and then, the necrotic tissue or the like can be contained within the collecting member 3.

Fourth Embodiment

Figure 20:
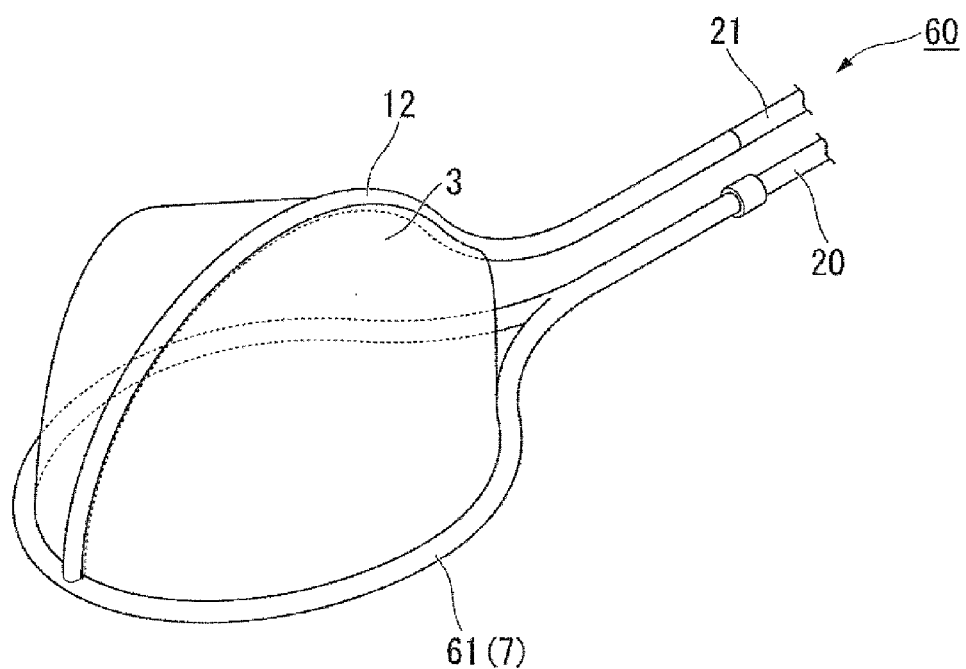
FIG. 20 is a perspective view showing a treatment instrument of a fourth embodiment of the invention.
Figure 21:
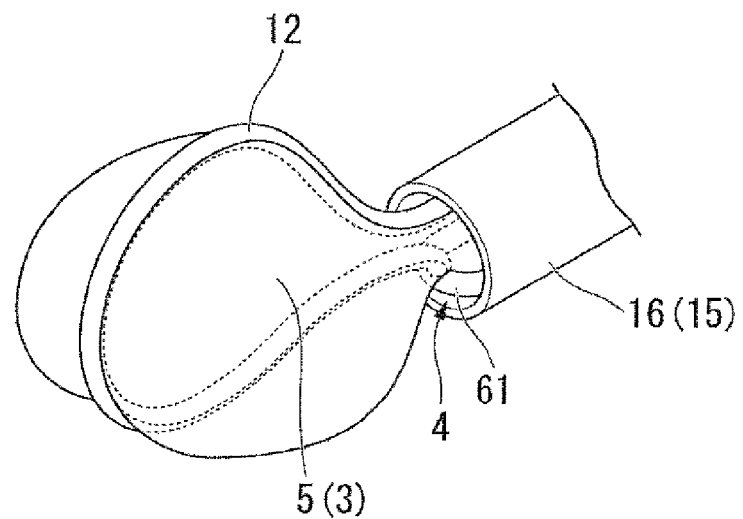
FIG. 21 is a perspective view showing the treatment instrument of the fourth embodiment of the invention.
Figure 22:
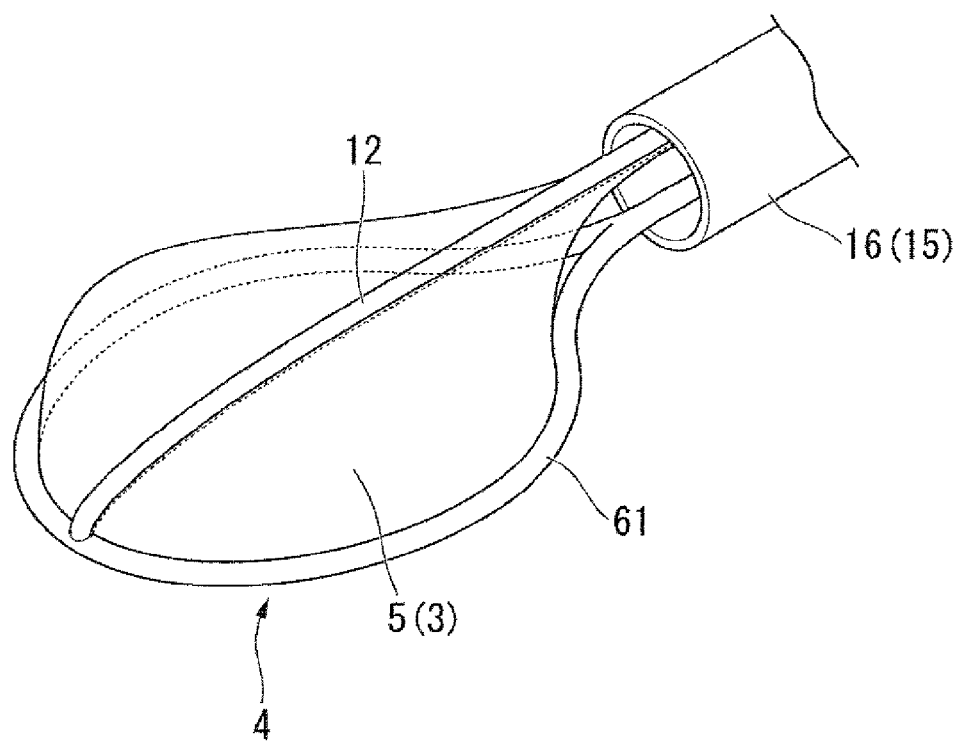
FIG. 22 is a perspective view showing the treatment instrument of the fourth embodiment of the invention.

Next, a treatment instrument of a fourth embodiment of the invention will be described. FIG. 20 is a perspective view showing the configuration of a portion of the treatment instrument of the present embodiment. FIGS. 21 and 22 are views for describing the operation of the treatment instrument of the present embodiment.

As shown in FIG. 20, the treatment instrument 60 has a snare 61 that is formed from an elastic wire that can cut a necrotic tissue or the like, as the frame part 7. The collecting member 3 is attached to the snare 61. Additionally, the distal end of the volume adjusting member 12 is fixed to a distal end of the elastic wire that constitutes the snare 61. The snare 61 may be constituted by a plate loop.

Even in such a configuration, as shown in FIG. 21, the opening portion 4 of the collecting member 3 can be closed by pulling the snare 61 into the longitudinal-axis member 16. Additionally, as shown in FIG. 22, by pulling the volume adjusting member 12 into the longitudinal-axis member 16 when the snare 61 has come out of the distal end of the longitudinal-axis member 16, the volume of the containing portion 5 of the collecting member 3 can be made small. This exhibits the same effects as the respective treatment instruments described in the above first to third embodiments.

Additionally, in the treatment instrument 60 of the present embodiment, a necrotic tissue or the like can be cut by the snare 61.

Fifth Embodiment

Figure 23:
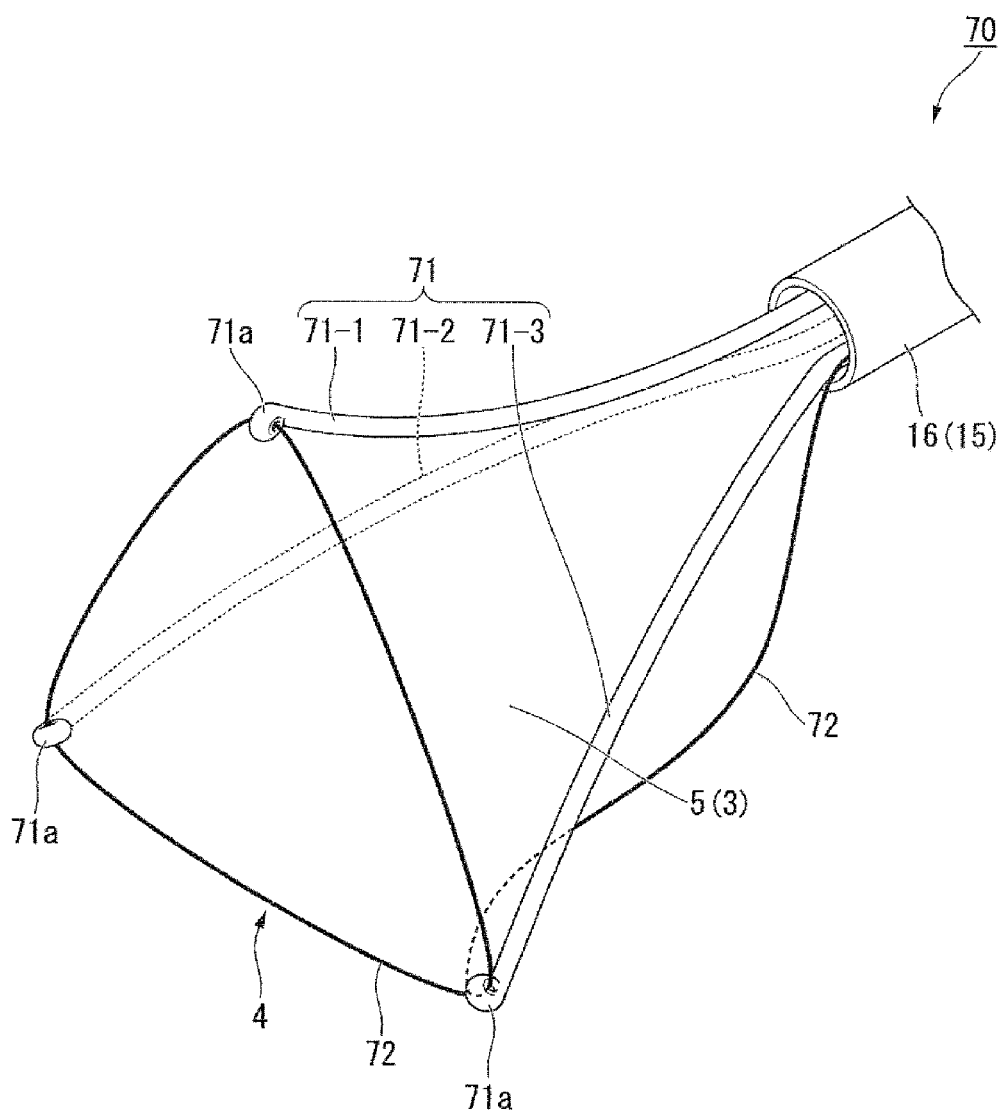
FIG. 23 is a perspective view showing a treatment instrument of a fifth embodiment of the invention.
Figure 24:
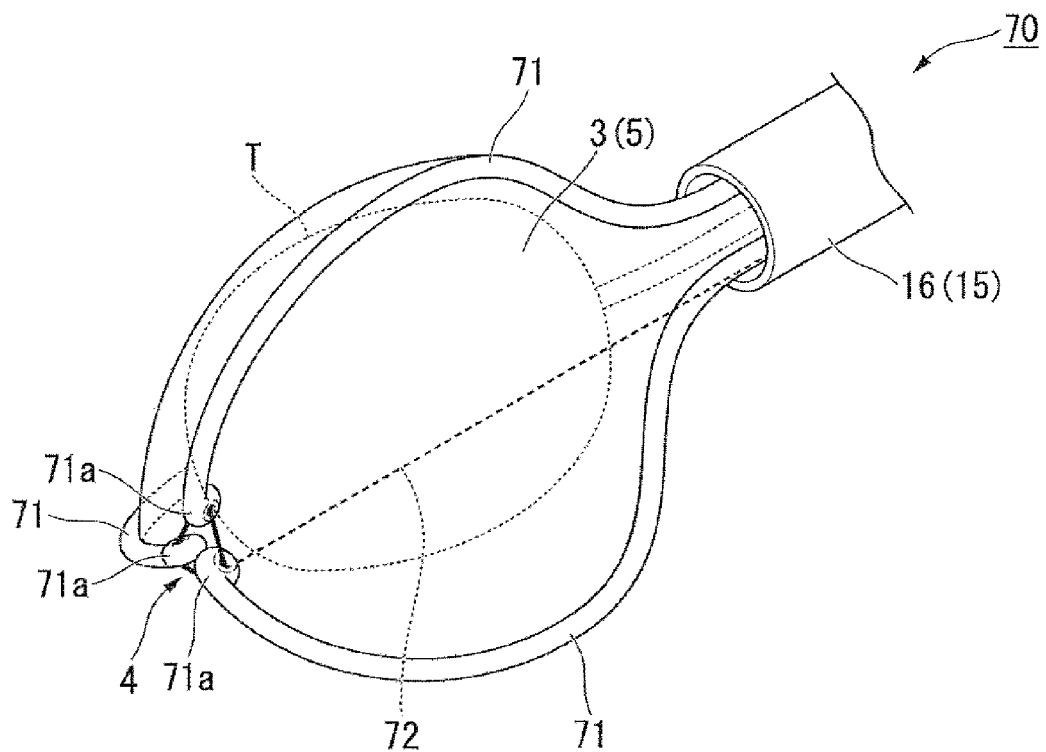
FIG. 24 is a perspective view showing the treatment instrument of the fifth embodiment of the invention.

Next, a treatment instrument of a fifth embodiment of the invention will be described. FIG. 23 is a perspective view showing the configuration of a portion of the treatment instrument of the present embodiment. FIG. 24 is a view for describing the operation of the treatment instrument of the present embodiment.

As shown in FIG. 23, in the treatment instrument 70, the frame part 7 is constituted by leg portions 71 (a leg portion 71-1, a leg portion 71-2, and a leg portion 71-3) that are formed from three elastic wires bent so that distal ends of the leg portions are spaced apart from each other. Through holes 71a are formed in respective distal ends of the elastic wires that constitute the leg portions 71.

A threadlike member 72 is attached to the through holes 71a formed in the respective elastic wires that constitute the leg portions 71. The threadlike member 72 is fixed to the slider 33-2 through the longitudinal-axis member 16. That is, in the present embodiment, the threadlike member 72 exhibits the same function as the opening operating member 20 described in the first embodiment.

The collecting member 3 is attached to the respective elastic wires of the leg portions 71 when the opening portion 4 is turned to the distal end side and the deepest portion of the containing portion 5 is turned to the proximal end side. The distal ends of the leg portions 71 are located in the opening portion 4 of the collecting member 3, and the threadlike member 72 is attached along the edge of the opening portion 4.

In the present embodiment, the collecting member 3 is housed inside the longitudinal-axis member 16 when the frame part 7 is pulled into the longitudinal-axis member 16. Additionally, if the frame part 7 is delivered from the distal end of the longitudinal-axis member 16, the opening portion 4 of the collecting member 3 expands by restoring forces of the respective elastic wires that constitute the leg portions 71. In addition, as the respective elastic wires are restored so that the distal ends of the leg portions 71 expand, the threadlike member 72 fixed to the slider 33-2 may be moved to the distal end side along the longitudinal axis of the longitudinal-axis member 16.

If a necrotic tissue or the like is contained in the containing portion 5 of the collecting member 3, the slider 33-2 is moved to the proximal end side of the shaft portion 32-2 by an operator (refer to FIG. 2). Thereby, the threadlike member 72 is moved to the proximal end side, and the respective elastic wires are elastically deformed so that the distal ends of the respective elastic wires of the leg portions 71 approach each other (refer to FIG. 24). Since the necrotic tissue T or the like is contained inside the collecting member 3, the three elastic wires are curved in a shape that wraps the outside of the necrotic tissue T or the like.

The opening portion 4 of the collecting member 3 is closed when the distal ends of the leg portion 71 touch each other. In this state, an operator allows the necrotic tissue or the like contained in the collecting member 3 to move.

In a case where the necrotic tissue or the like contained in the collecting member 3 is taken out of the collecting member 3, first, the slider 33-2 is moved to the distal end side of the shaft portion 32-2 so as to release the traction force of the threadlike member 72. Then, the distal ends of the elastic wires are spaced apart from each other by the restoring forces of the respective elastic wires that constitute the leg portions 71. Moreover, the slider 33-1 is moved to the proximal end side of the shaft portion 32-1 by an operator, and the respective elastic wires are pulled into the longitudinal-axis member 16 from the proximal end side. Then, the containing portion 5 of the collecting member 3 is also pulled into the longitudinal-axis member 16 from the proximal end side (deepest portion side of the containing portion 5), and the volume of the containing portion 5 becomes gradually smaller. Thereby, the necrotic tissue or the like contained in the containing portion 5 is moved to the distal end side, that is, the opening portion 4 of the collecting member 3, and is pushed out to the outside of the collecting member 3 from the opening portion 4.

In this way, in the present embodiment, the respective elastic wires that constitute the leg portions 71 function as the volume adjusting member for adjusting the volume of the containing portion 5.

The present embodiment also exhibits the same effects as the respective treatment instruments of the above-described first to fourth embodiments.

Additionally, in the treatment instrument 70 of the present embodiment, the opening portion 4 is turned to the distal end side. Thus, a collection target can be easily contained in the containing portion 5 by pushing the treatment instrument 70 into the distal end side of the treatment instrument channel 502 when the collection target is reflected within the endoscope image.

In addition, by operating one or a plurality of elastic wires in the leg portions 71 that are constituted by a plurality of elastic wires, independently from the other elastic wires, the one or the several elastic wires can also be configured so as to function solely as the volume adjusting member.

Modified Example 5-1

Figure 25:
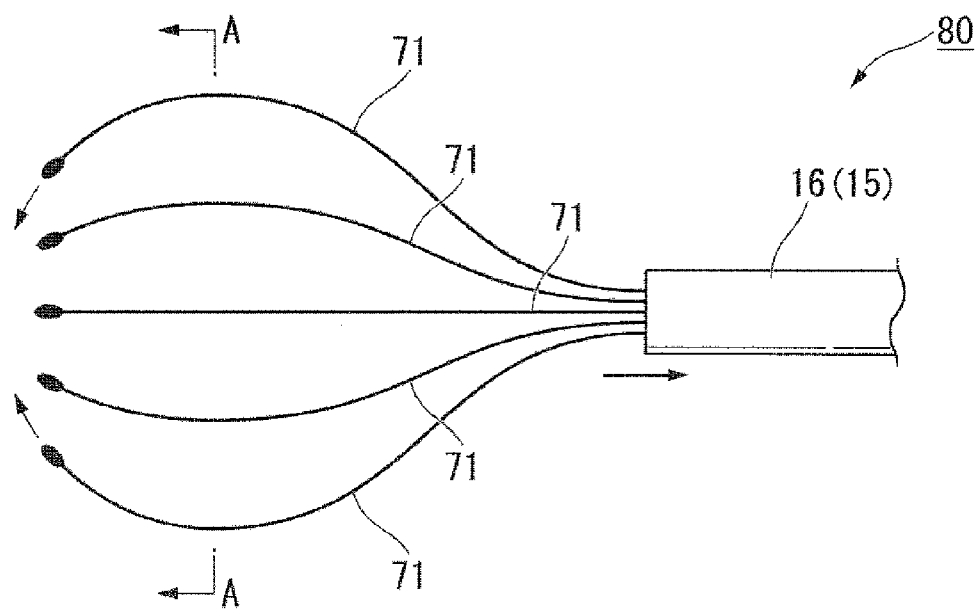
FIG. 25 is a perspective view showing the configuration of Modified Example 5-1 of the fifth embodiment of the invention.
Figure 26:
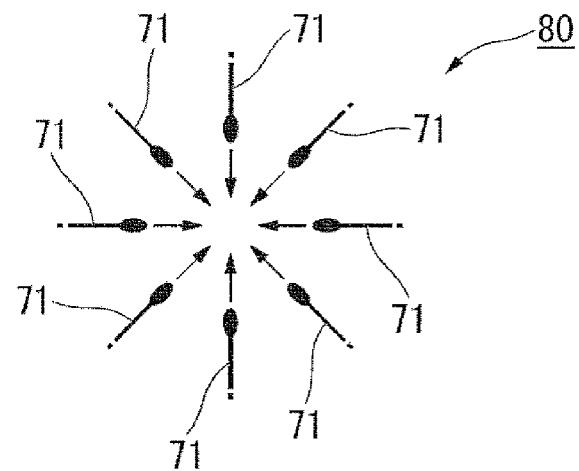
FIG. 26 is a cross-sectional view along line A-A of FIG. 25.

Next, Modified Example 5-1 of the present embodiment will be described. FIG. 25 is a perspective view showing the configuration of the present modified example. FIG. 26 is a cross-sectional view along line A-A of FIG. 25.

As shown in FIGS. 25 and 26, a treatment instrument 80 of the present modified example does not include the threadlike member 72. Moreover, in the treatment instrument 80, three or more (for example, seven) elastic wires that constitute the leg portions 71 are provided. In the present modified example, as the leg portions 71 are constituted by a number of elastic wires, the same functions as one having the collecting member 3 are exhibited. That is, the leg portions 71 can hold a necrotic tissue by a number of elastic wires.

Additionally, the respective elastic wires that constitute the leg portions 71 are bundled and fixed at proximal ends thereof. Moreover, the respective elastic wires are spaced farthest from each other at the intermediate portions of the respective elastic wires. The respective elastic wires are curved at the distal ends of the elastic wires so that the interval between the respective elastic wires becomes shorter than at the intermediate portions. Additionally, the distal ends of the respective elastic wires are formed in a substantially spherical shape, and prevent the respective elastic wires from being unintentionally stuck into a tissue.

If the leg portions 71 constituted by the respective elastic wires are pulled into the longitudinal-axis member 16, a space for containing a necrotic tissue or the like is located at the intermediate portions of the respective elastic wires of the leg portions 71, and the distal ends of the respective elastic wires are closed. Thereby, a necrotic tissue or the like can be gripped by the distal ends of the respective elastic wires, or a necrotic tissue or the like can be contained into a space formed by the respective elastic wires and then, the necrotic tissue or the like can be moved.

Sixth Embodiment

Figure 27:
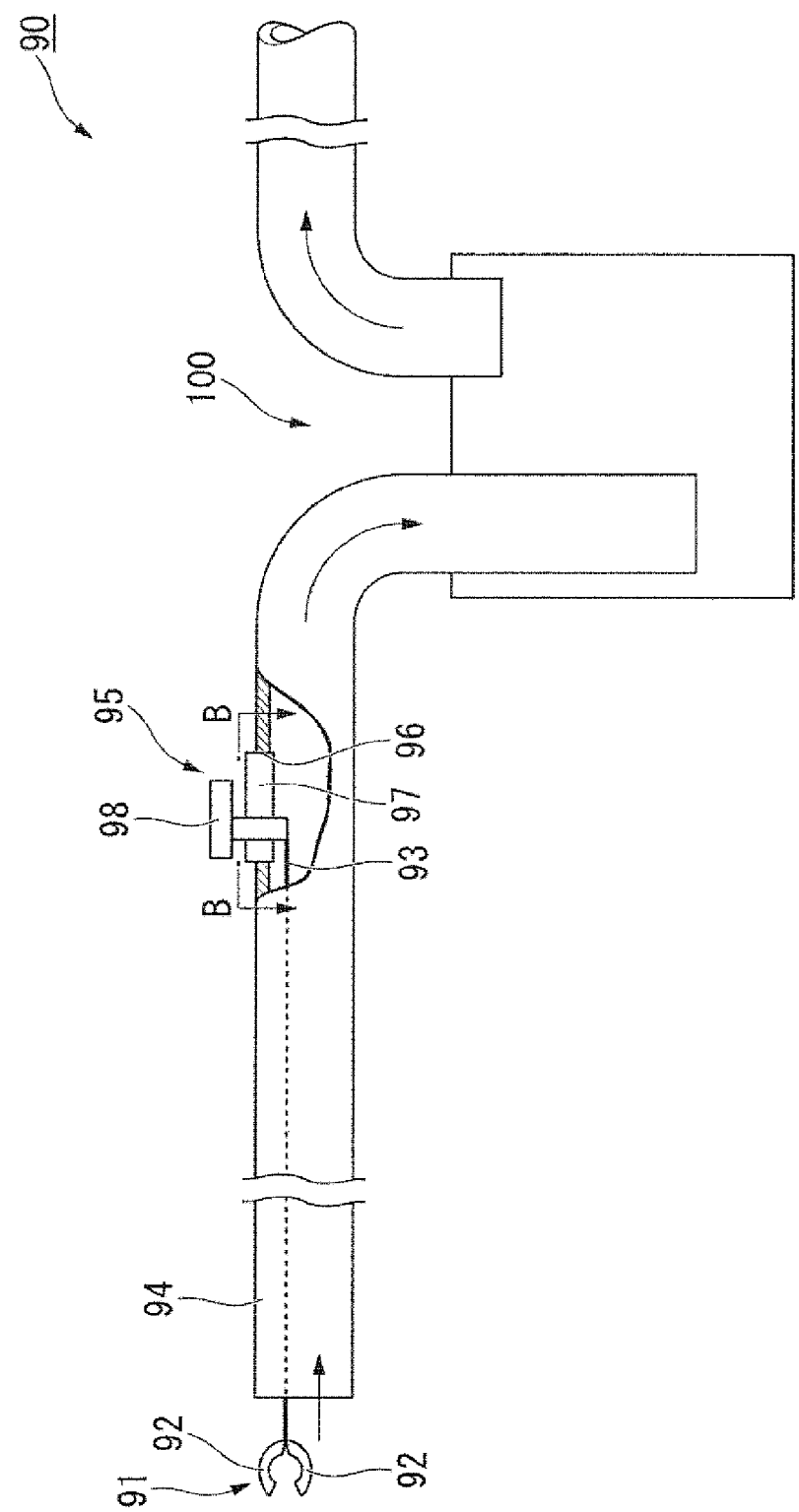
FIG. 27 is an overall view showing a treatment instrument of a sixth embodiment of the invention.
Figure 28:
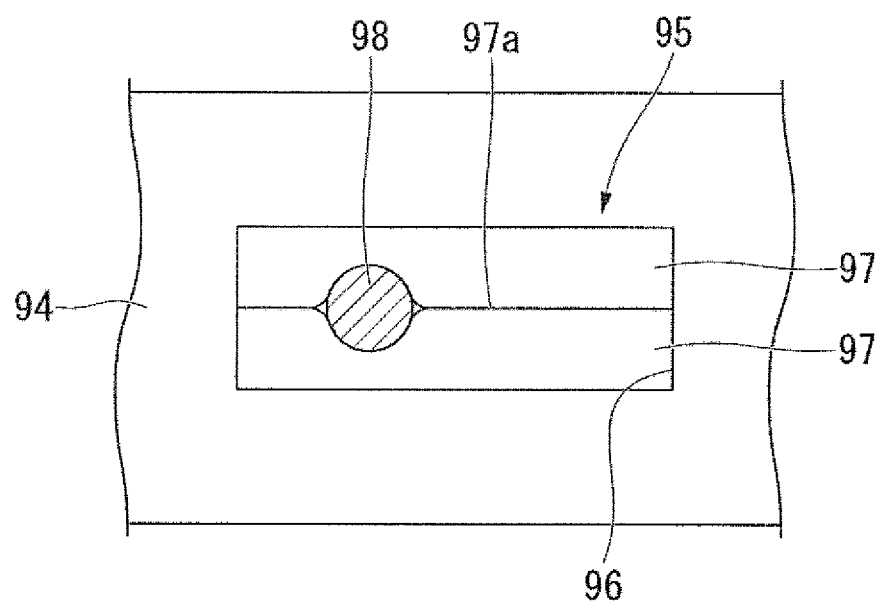
FIG. 28 is a cross-sectional view along line B-B of FIG. 27.

Next, a treatment instrument of a sixth embodiment of the invention will be described. FIG. 27 is an overall view showing the treatment instrument of the present embodiment. FIG. 28 is a cross-sectional view along line B-B of FIG. 27.

As shown in FIGS. 27 and 28, a treatment instrument 90 of the present embodiment includes a treatment section 91 that performs a treatment within the body, an operating wire 93, a tubular longitudinal-axis member 94, and an operation portion 95. The operating wire 93 operates the treatment section 91 that has the treatment section 91 attached to a distal end thereof. The tubular longitudinal-axis member 94 has the operating wire 93 inserted therethrough, and has the treatment section 91 arranged on a distal end side thereof. The operation portion 95 is provided at an intermediate portion of the longitudinal-axis member 94.

The treatment section 91 has a pair of openable and closable gripping portions 92. A tissue can be gripped by the gripping portions 92.

The operating wire 93 is a flexible linear member that has a proximal end attached to the operation portion 95 and has a distal end attached to the treatment section 91. As the operating wire 93 is advanced and retracted, the pair of gripping portions 92 is opened and closed.

The longitudinal-axis member 94 is a member that has flexibility such that the longitudinal-axis member can be inserted into the treatment instrument channel 502 (refer to FIG. 1) of the endoscope apparatus 500. The longitudinal-axis member 94 has a through hole in which a cross-section orthogonal to the central axis is formed in a circular shape. The shape of the through hole is formed in the same shape in any place in the direction of the central axis of the longitudinal-axis member 94. The proximal end of the longitudinal-axis member 94 is connected to a suction device 100 that suctions a body fluid or a tissue. That is, the treatment instrument 90 of the present embodiment can take out a body fluid or a tissue to the outside of the body by suctioning the body fluid or the tissue from the distal end thereof and moving the body fluid or the tissue to the suction device 100.

The operation portion 95 includes a long hole portion 96, an airtight member 97, and an operating member 98. The long hole portion 96 is formed in the longitudinal-axis member 94 so that a portion of an outer wall of the longitudinal-axis member 94 is passed therethrough, and is long in the direction of the central axis of the longitudinal-axis member 94. The airtight member 97 is attached to the long hole portion 96, and has a slit 97a formed therein. The operating member 98 is fixed to a proximal end of the operating wire 93 while being inserted through the slit 97a of the airtight member 97. The distance from the distal end of the longitudinal-axis member 94 to the operation portion 95 is longer than the total length of the treatment instrument channel 502.

As shown in FIG. 28, the slit 97a formed in the airtight member 97 is formed so as to be long in a direction parallel to the longitudinal axis of the longitudinal-axis member 94. The airtight member 97 has the slit 97a brought into a closed state due to its own elasticity, and is configured so that the airtight state of the slit 97a is maintained even if the operating member 98 inserted through the slit 97a of the airtight member 97 is advanced and retracted along the slit 97a.

The treatment section 91 can be opened and closed by moving the operating member 98 in the direction of the central axis of the longitudinal-axis member 94.

The operation of the treatment instrument 90 will be described.

When the treatment instrument 90 is used, the longitudinal-axis member 94 is inserted through the treatment instrument channel 502 from the distal end side of the longitudinal-axis member 94, and the longitudinal-axis member 94 is delivered from the distal end of the treatment instrument channel 502. At this time, the operation portion 95 does not reach a proximal end of the treatment instrument channel 502. That is, the operation portion 95 is located out of the treatment instrument channel 502. For this reason, the distal end of the longitudinal-axis member 94 is located ahead of the distal end face of the insertion section 501 of the endoscope apparatus 500.

Next, an operator of the treatment instrument 90 performs a proper treatment, such as moving or excising a tissue using the treatment section 91.

Next, the operator drives the suction device 100 and suctions a body fluid or a tissue into the longitudinal-axis member 94 from the distal end of the longitudinal-axis member 94. In this case, although it is necessary to bring the distal end of the longitudinal-axis member 94 into contact with or close to a suction target, since the distal end of the longitudinal-axis member 94 is located ahead of the distal end face of the endoscope apparatus 500, the distal end face does not contact the suction target, and the distance at which the suction target can be conveniently observed is maintained. For this reason, the operator can suction the suction target while observing the suction target.

Additionally, since the long hole portion 96 is sealed by the airtight member 97 and the slit 97a formed in the airtight member 97 is also configured in a sealing state due to the elasticity of the airtight member 97, a gas does not enter the longitudinal-axis member 94 through the slit 97a even if the inside of the longitudinal-axis member 94 is brought into a negative-pressure state by an suction device 100.

Additionally, the invention is not limited to a case where the cross-sectional shape of the treatment instrument channel 502 of the endoscope apparatus 500 is always the same shape in the longitudinal direction. For example, a case where there is a level difference or the like in the treatment instrument channel 502 is also considered. A place where the cross-sectional shape of the treatment instrument channel 502 varies is a portion in which the suctioned tissue is easily caught. If the tissue is caught in such a portion, the treatment instrument channel 502 may be clogged.

In the present embodiment, the tissue suctioned by the suction device 100 is collected through the longitudinal-axis member 94. The longitudinal-axis member 94 is a tubular member that is formed with a through hole in which a cross-sectional shape from the distal end to the proximal end is the same shape or a shape becomes thick from the distal end to the proximal end. Therefore, the inside of the longitudinal-axis member 94 has no level difference such that a tissue is caught, and is not easily clogged by the tissue.

Modified Example 6-1

Figure 29:
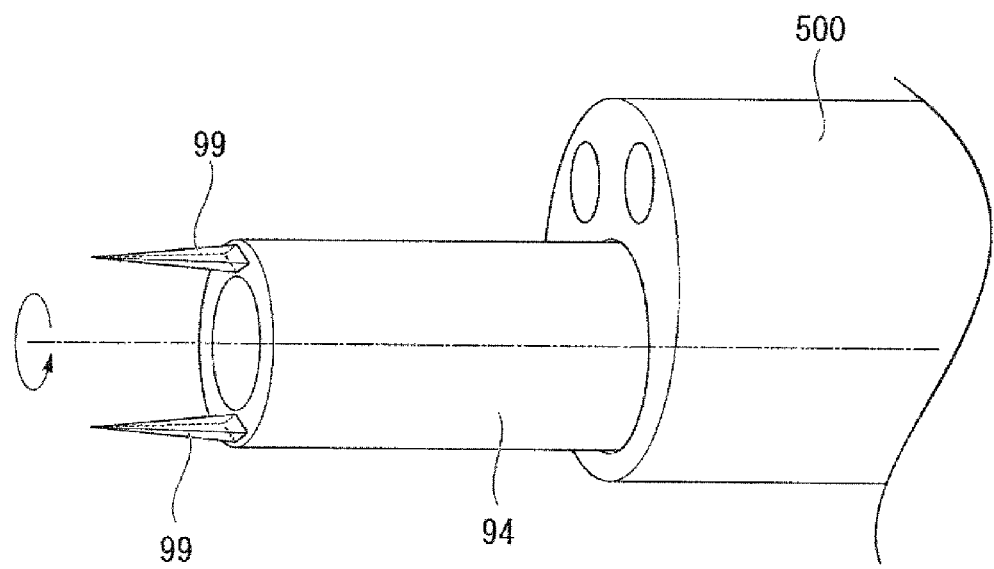
FIG. 29 is a side view showing the configuration of Modified Example 6-1 of the sixth embodiment of the invention.

Next, the configuration of Modified Example 6-1 of the present embodiment will be described. FIG. 29 is a perspective view showing the configuration of the present modified example.

As shown in FIG. 29, in the present modified example, the configuration of the treatment section 91 is different from that of the sixth embodiment. In the present modified example, a pair of dual-head needles 99 that extend from the distal end of the longitudinal-axis member 94 toward the front are provided at the distal end of the longitudinal-axis member 94, in, addition to the above-described gripping portions 92.

The dual-head needles 99 have thin and sharp distal ends so as to be capable of puncturing a tissue. Additionally, a cutting blade that cuts a tissue is provided at a side portion of the dual-head needle 99. The dual-head needles 99 are stuck into a tissue by pushing out the longitudinal-axis member 94 to the front, and if the longitudinal-axis member 94 is further rotated around the central axis, the tissue is cut in a columnar shape by the cutting blade. In the present modified example, the tissue cut in a columnar shape can be suctioned into the longitudinal-axis member 94 and can be moved to the outside of the body.

Modified Example 6-2

Figure 30:
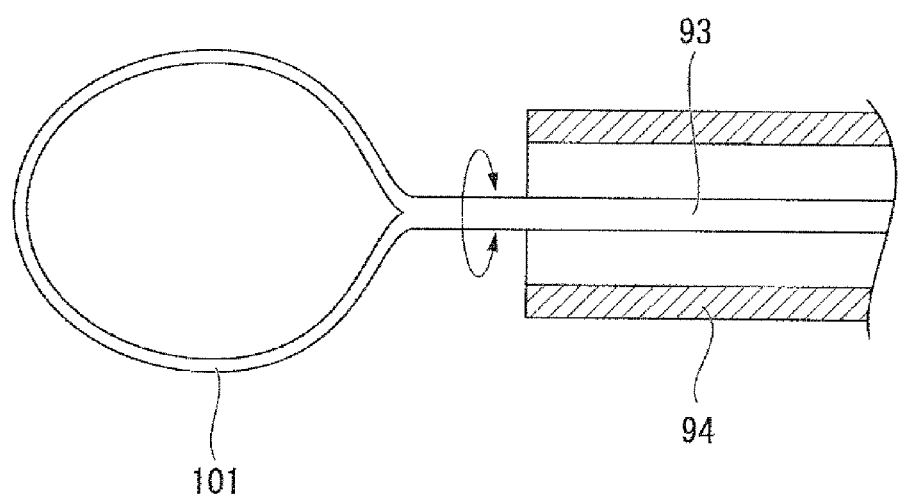
FIG. 30 is a side view showing the configuration of Modified Example 6-2 of the sixth embodiment of the invention.

Next, the configuration of Modified Example 6-2 of the present embodiment will be described. FIG. 30 is a partial cross-sectional view showing the configuration of the present modified example.

As shown in FIG. 30, in the present modified example, the configuration of the treatment section 91 is different from that of the sixth embodiment. In the present modified example, a wire loop 101 fixed to the distal end of the operating wire 93 is provided instead of the above-described gripping portions 92.

The wire loop 101 is formed from a linear member made of resin materials, such as a polyamide synthetic fiber (for example, nylon (registered trademark)), and has rigidity such that a loop shape is maintained when a necrotic tissue is raked out.

In the present modified example, if the longitudinal-axis member 94 is rotated around the central axis of the longitudinal-axis member 94, the operation portion 95 also rotates integrally with the longitudinal-axis member 94, and the operating wire 93 attached to the operation portion 95 also rotates integrally with the longitudinal-axis member 94. Thereby, the wire loop 101 fixed to the distal end of the operating wire 93 also rotates integrally with the longitudinal-axis member 94.

Additionally, if the operating member 98 is moved to the proximal end side of the longitudinal-axis member 94, a proximal end portion of the wire loop 101 is pulled into the longitudinal-axis member 94, and the size of the loop becomes small. In this way, the loop diameter of the wire loop 101 can be adjusted by advancing and retracting the operating member 98 in the direction of the central axis of the longitudinal-axis member 94.

Modified Example 6-3

Figure 31:
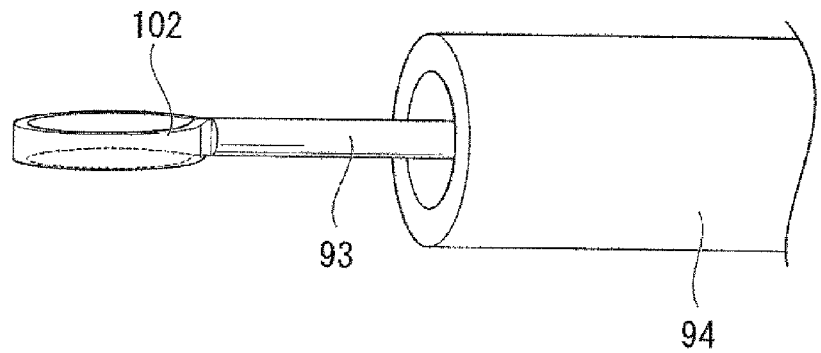
FIG. 31 is a side view showing the configuration of Modified Example 6-3 of the sixth embodiment of the invention.

Next, the configuration of Modified Example 6-3 of the present embodiment will be described. FIG. 31 is a perspective view showing the configuration of the present modified example.

As shown in FIG. 31, in the present modified example, a plate loop 102 fixed to the distal end of the operating wire 93 is provided instead of the above-described gripping portions 92.

The plate loop 102 is a member formed in a loop shape by fixing both ends of a plate-like sheet member having flexibility to each other. A fixing portion of the sheet member of the plate loop 102 is fixed to the distal end of the operating wire 93.

In the present modified example, if the longitudinal-axis member 94 is rotated around the central axis of the longitudinal-axis member 94 similar to the above Modified Example 6-2, the plate loop 102 can be rotated. Additionally, in the present modified example, if the operating member 98 is advanced and retracted in the direction of the central axis of the longitudinal-axis member 94, the loop diameter of the plate loop 102 can be adjusted. Moreover, the plate loop 102 of the present modified example has higher rigidity than the wire loop 101 described in the above-described modified example 6-2, and a necrotic tissue or the like can be shaved off by both ends of the plate loop 102 in the lateral direction.

Modified Example 6-4

Figure 32:
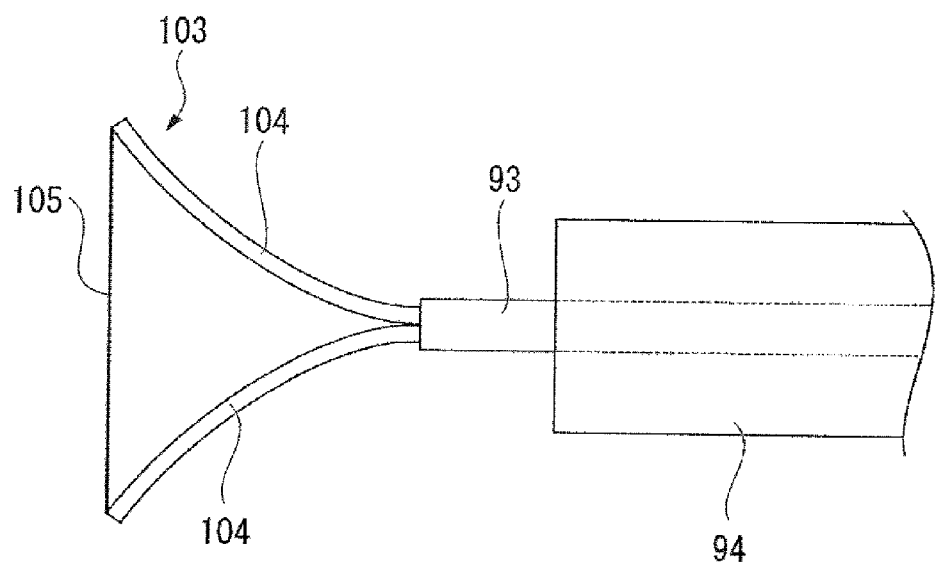
FIG. 32 is a side view showing the configuration of Modified Example 6-4 of the sixth embodiment of the invention.

Next, the configuration of Modified Example 6-4 of the present embodiment will be described. FIG. 32 is a side view showing the configuration of the present modified example.

As shown in FIG. 32, the present modified example is different from a sixth embodiment in that a treatment section 103 is provided instead of the treatment section 91. The treatment section 103 includes a pair of elastic wires 104 that are curved so that distal ends of the elastic wires open to each other, and a linear member 105 that connects the distal ends of the respective elastic wires 104. The treatment section 103 is fixed to the distal end of the operating wire 93.

The linear member 105 is made of for example, resin materials, such as a polyamide synthetic fiber, similar to the linear member that constitutes the wire loop 101 described in the above-described Modified Example 6-2.

In the present modified example, since the angle formed between the elastic wires 104 and the linear member 105 is an acute angle, a necrotic tissue or the like in a narrow gap can be raked out by connecting portions between the elastic wires 104 and the linear member 105.

Modified Example 6-5

Figure 33:
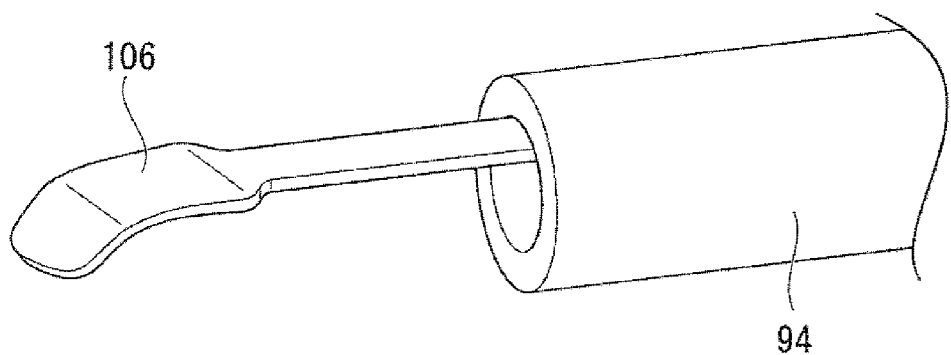
FIG. 33 is a side view showing the configuration of Modified Example 6-5 of the sixth embodiment of the invention.

Next, the configuration of Modified Example 6-5 of the present embodiment will be described. FIG. 33 is a perspective view showing the configuration of the present modified example.

As shown in FIG. 33, in the present modified example, a spatula member 106 that extends forward from the distal end of the longitudinal-axis member 94 is provided in addition to the above-described gripping portions 92.

The spatula member 106 has a shape that is curved in a direction approaching the central axis of the longitudinal-axis member 94, at the distal end thereof.

In the present modified example, a necrotic tissue or the like can be raked out using the spatula member 106, the raked-out necrotic tissue is located near the opening of the distal end of the longitudinal-axis member 94, and is pulled into the longitudinal-axis member 94 by a suction force generated by the suction device 100.

Modified Example 6-6

Figure 34:
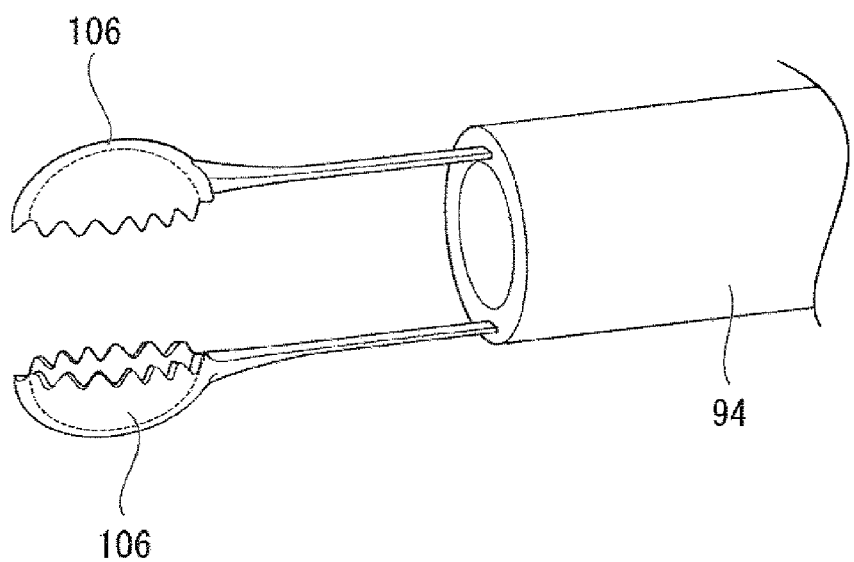
FIG. 34 is a side view showing the configuration of Modified Example 6-6 of the sixth embodiment of the invention.

Next, the configuration of Modified Example 6-6 of the present embodiment will be described. FIG. 34 is a side view showing the configuration of the present modified example.

As shown in FIG. 34, in the present modified example, spatula members 106 described in the above-described Modified Example 6-5 are provided in two places that face each other in the radial direction at the distal end of the longitudinal-axis member 94. Additionally in the present modified example, each spatula member 106 has a spoon-like recess at the distal end thereof. Thereby, a necrotic tissue or the like can be pinched between the spatula members 106 provided in two places that face each other, and the necrotic tissue or the like can be gripped.

Modified Example 6-7

Figure 35:
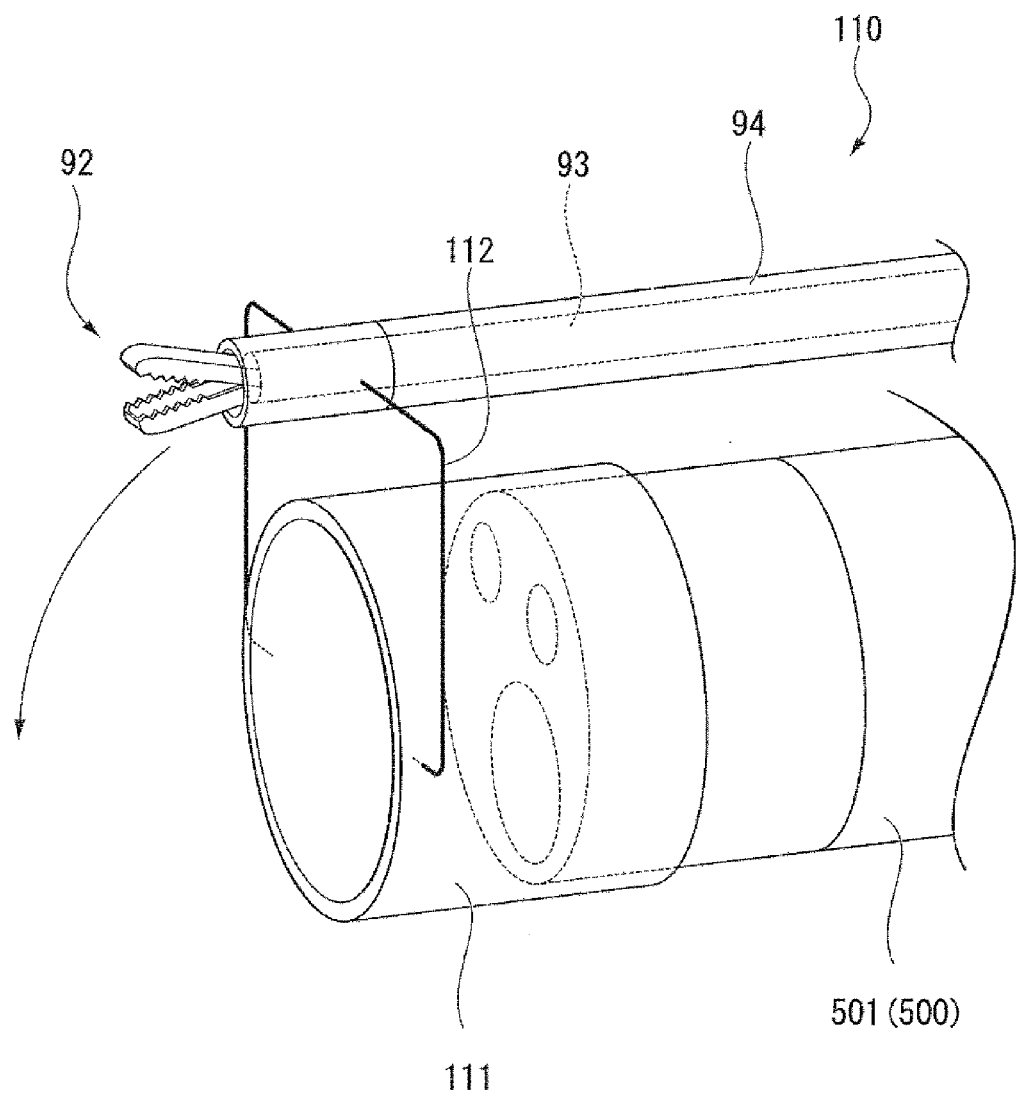
FIG. 35 is a side view showing the configuration of Modified Example 6-7 of the sixth embodiment of the invention.

Next, the configuration of Modified Example 6-7 of the present embodiment will be described. FIG. 35 is a perspective view showing the configuration of the present modified example.

As shown in FIG. 35, a treatment instrument 110 of the present modified example can be attached to the outside of the insertion section 501 of the endoscope apparatus 500.

The treatment instrument 110 includes a cylindrical cap 111 that can be attached to the distal end of the insertion section 501 of the endoscope apparatus 500, and a link wire 112 that connects the distal end of the longitudinal-axis member 94 and the cap 111. Additionally, the treatment instrument 110 has the gripping portions 92, the operating wire 93, and the operation portion 95 (not shown), similar to the above-described sixth embodiment.

In the present modified example, if the longitudinal-axis member 94 is moved to the proximal end side, the distal end of the longitudinal-axis member 94 is guided to a position adjacent to a side surface of the insertion section 501 of the endoscope apparatus 500 by the link wire 112 provided at the distal end of the longitudinal-axis member 94. Additionally, if the longitudinal-axis member 94 is moved to the distal end side, the treatment section 91 is guided by the link wire 112 so that the treatment section 91 moves toward the center of the visual field of the endoscope apparatus 500.

In the present modified example, a body fluid or a tissue can also be suctioned through the longitudinal-axis member 94, and the body fluid or the tissue can also be suctioned through the treatment instrument channel 502 of the endoscope apparatus 500.

Additionally, since the treatment instrument 110 is configured so as to be attached to the outside of the insertion section 501 of the endoscope apparatus 500, the dimensions of respective portions of the treatment instrument 110 are not restricted by the internal diameter of the treatment instrument channel 502 of the endoscope apparatus 500. For this reason, as the endoscope apparatus 500, the endoscope apparatus 500 in which the internal diameter of the treatment instrument channel 502 is small, or the endoscope apparatus 500 that does not include the treatment instrument channel 502, or the like can be adopted.

Seventh Embodiment

Figure 36:
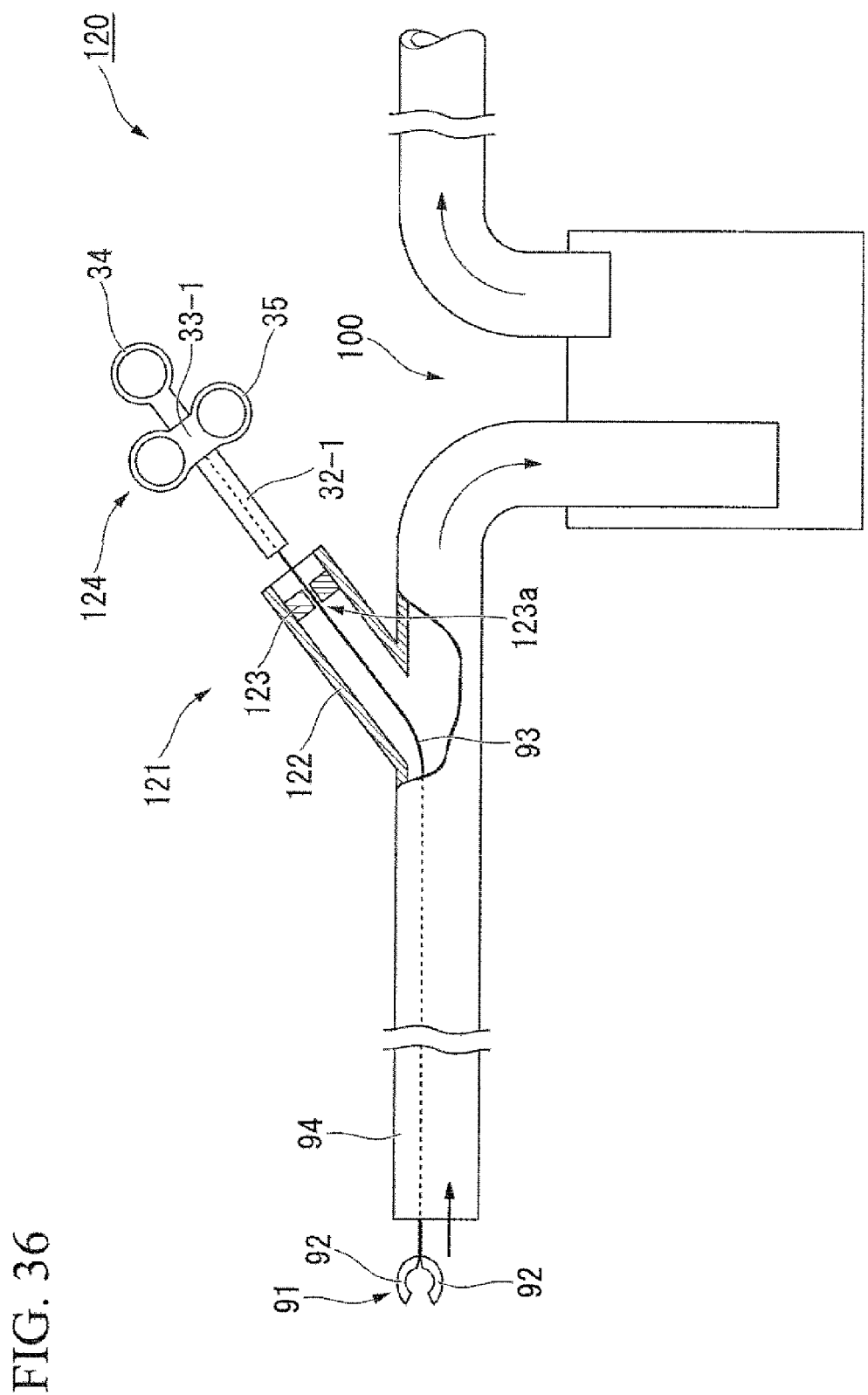
FIG. 36 is an overall view showing the configuration of a portion of a treatment section of a seventh embodiment of the invention.

Next, a treatment instrument of a seventh embodiment of the invention will be described. FIG. 36 is an overall view showing the configuration of a portion of the treatment instrument of the present embodiment.

As shown in FIG. 36, the treatment instrument 120 of the present embodiment is different from that of the above-described sixth embodiment in that an operation portion 121 is provided instead of the operation portion 95.

The operation portion 121 includes a bypass 122, an airtight member 123, and an operating body portion 124. The bypass 122 is formed so as to branch from the longitudinal-axis member 94 toward a direction intersecting the central axis of the longitudinal-axis member 94. The airtight member 123 is provided within the bypass 122, and has the operating wire 93 inserted therethrough. The operating body portion 124 is connected to the proximal end of the operating wire 93.

The bypass 122 has an inclination angle at which a proximal end side of the bypass 122 faces the proximal end side of the longitudinal-axis member 94.

The airtight member 123 is an elastic member that is fixed to the inner surface of the bypass 122 in an airtight state, and has a through hole 123*a* through which the operating wire 93 is inserted so as to be capable of advancing and retracting. The through hole 123*a* formed in the airtight member 123 has an internal diameter dimension slightly smaller than the external diameter dimension of the operating wire 93, and the airtight member 123 and the operating wire 93 are configured so as to slide while maintaining an airtight state.

The operating body portion 124 has the same configuration as the operating body portion 31-1 described in the first embodiment. That is, the operating body portion 124 has the rod-shaped shaft portion 32-1 and the slider 33-1 that is attached to the shaft portion 32-1.

Even in the treatment instrument 120 of the present embodiment, similar to the treatment instrument described in above-described sixth embodiment, the proximal end of the longitudinal-axis member 94 is connected to the suction, device 100 so that a body fluid, a tissue, or the like can be suctioned from the distal end of the longitudinal-axis member 94. At this time, since the airtight state is maintained by the airtight member 123 between the operating wire 93 and the airtight member 123 and between the airtight member 123 and the bypass 122, even if the inside of the longitudinal-axis member 94 is brought into a negative pressure state by the suction device 100, a gas does not enter the longitudinal-axis member 94 from the bypass 122.

Modified Example 7-1

Figure 37:
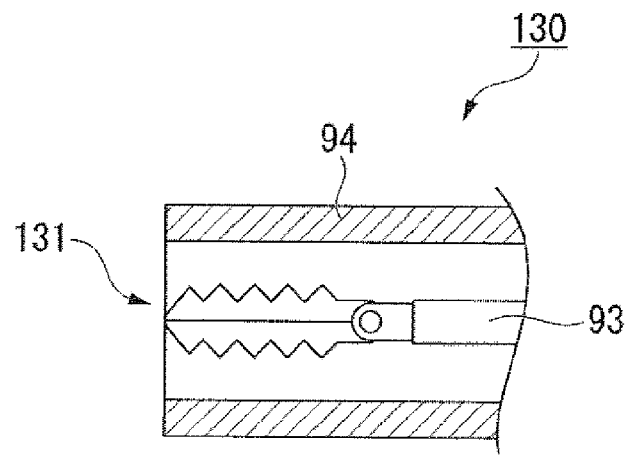
FIG. 37 is a partial cross-sectional view showing the configuration of Modified Example 7-1 of the seventh embodiment of the invention.
Figure 38:
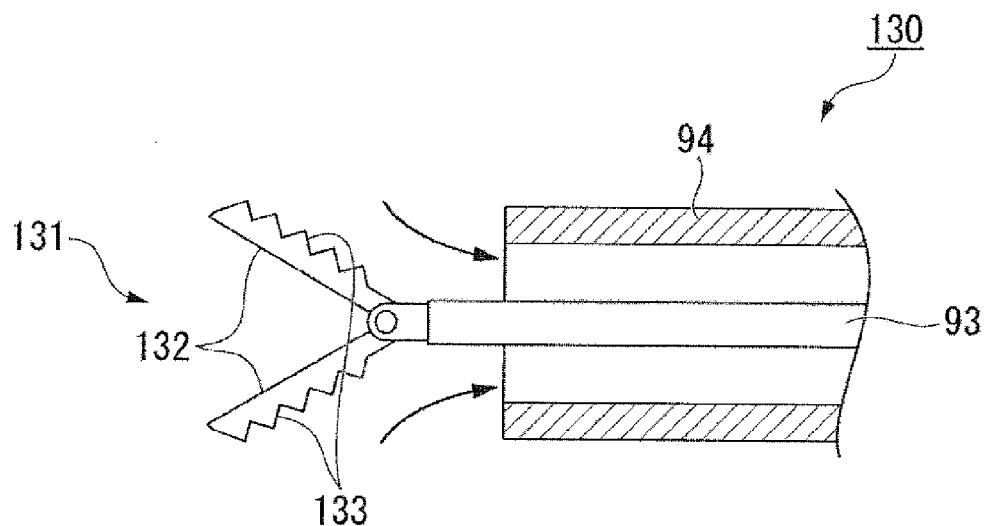
FIG. 38 is a partial cross-sectional view showing the configuration of Modified Example 7-1 of the seventh embodiment of the invention.

Next, the configuration of Modified Example 7-1 of the present embodiment will be described. FIGS. 37 and 38 are partial cross-sectional views showing the configuration of the present modified example.

As shown in FIGS. 37 and 38, a treatment instrument 130 of the present modified example is different from the above-described seventh embodiment in that this treatment instrument includes a treatment section 131 that is different from the configuration of the treatment section 91 (refer to the sixth embodiment).

The treatment section 131 of the present modified example is forceps in which a pair of surfaces 132 that face each other each other, and a pair of surfaces 133 that are mutually turned outward are formed in a saw shape.

The treatment section 131 of such a shape can bring the pair of surfaces 133 formed in a saw shape into contact with a necrotic tissue or the like, thereby raking out the necrotic tissue or the like.

In addition, the pair of surfaces 132 that face each other may be formed in a saw shape.

Modified Example 7-2

Figure 39:
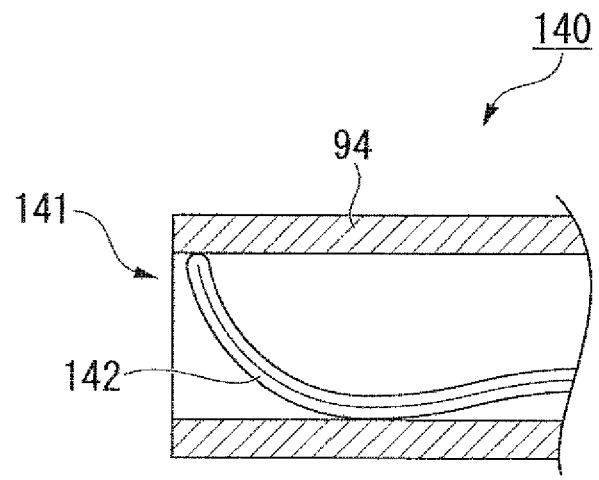
FIG. 39 is a partial cross-sectional view showing the configuration of Modified Example 7-2 of the seventh embodiment of the invention.
Figure 40:
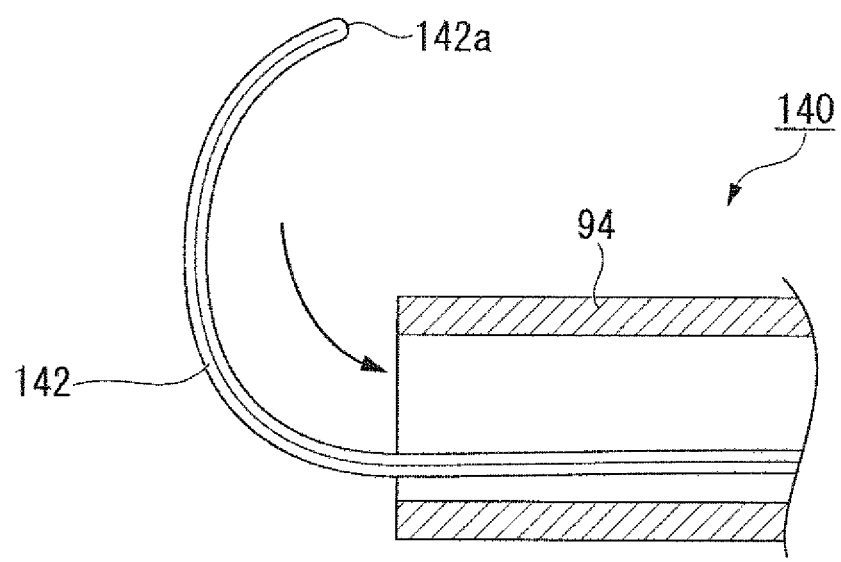
FIG. 40 is a partial cross-sectional view showing the configuration of Modified Example 7-2 of the seventh embodiment of the invention.

Next, the configuration of Modified Example 7-2 of the present embodiment will be described. FIGS. 39 and 40 are partial cross-sectional views showing the configuration of the present modified example.

As shown in FIGS. 39 and 40, a treatment instrument 140 of the present modified example is different from the above-described seventh embodiment in that this treatment instrument includes a treatment section 141 that is different from the configuration of the treatment section 91 (refer to the sixth embodiment).

The treatment section 141 of the present modified example has a spatula member 142 that is curved so as to have a circular-arc shape larger than the internal diameter dimension of the longitudinal-axis member 94 when an external force is not applied. The spatula member 142 is in a state where the spatula member is extended in the direction of the central axis of the longitudinal-axis member 94 when the spatula member is housed inside the longitudinal-axis member 94, and has a shape that is curved so that a distal end 142a of the spatula member 142 faces the proximal end side of the longitudinal-axis member 94 when the spatula member is delivered from the distal end of the longitudinal-axis member 94.

Thereby, a necrotic tissue or the like can be raked out by the spatula member 142.

In addition, in the present modified example, the slider 33-1 does not need to be provided in the operating body portion 124, and a proximal end of the spatula member 142 may be directly connected to the operating body portion 124. In this case, the operating body portion 124 can be advanced and retracted with respect to the longitudinal-axis member 94 so as to move the spatula member 142.

Modified Example 7-3

Figure 41:
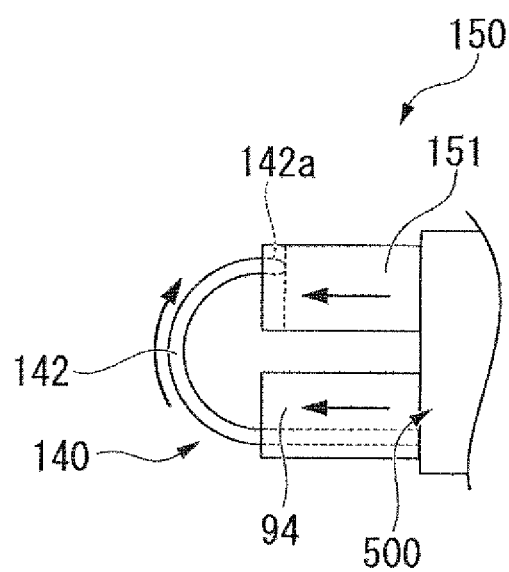
FIG. 41 is a side view showing the configuration of Modified Example 7-3 of the seventh embodiment of the invention.

Next, the configuration of Modified Example 7-3 of the present embodiment will be described. FIG. 41 is a side view showing the configuration of the present modified example.

As shown in FIG. 41, a treatment instrument 150 of the present modified example includes the treatment instrument 140 having the treatment section 141 shown in the above-described modified example 7-2, and a catheter tube 151.

The treatment instrument 140 and the catheter tube 151 are inserted through the respective treatment instrument channels 502 of the endoscope apparatus 500 including the two treatment instrument channels 502.

Additionally, the distal end 142a of the spatula member 142 delivered from the distal end of the longitudinal-axis member 94 of the treatment instrument 140 is configured so as to be inserted into the catheter tube 151 from the distal end of the catheter tube 151.

In the present modified example, the distal end 142a of the spatula member 142 is supported by the catheter tube 151. Thereby, when a necrotic tissue or the like is raked out by a curved portion of the spatula member 142, deflection of the spatula member 142 can be prevented. For this reason, the spatula member 142 can scoop out a necrotic tissue or the like with a stronger force.

Modified Example 7-4

Figure 42:
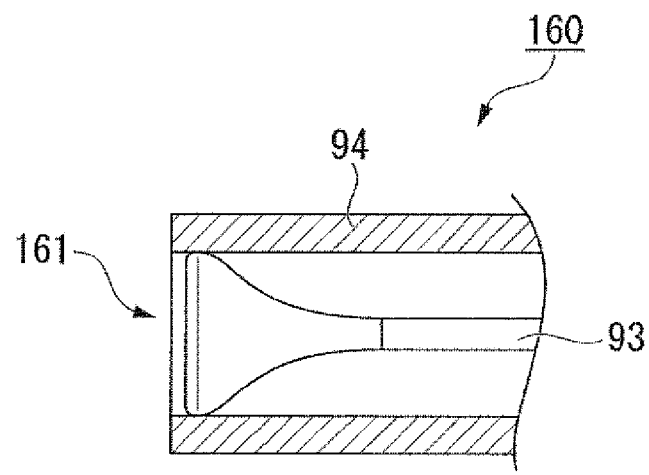
FIG. 42 is a partial cross-sectional view showing the configuration of Modified Example 7-4 of the seventh embodiment of the invention.
Figure 43:
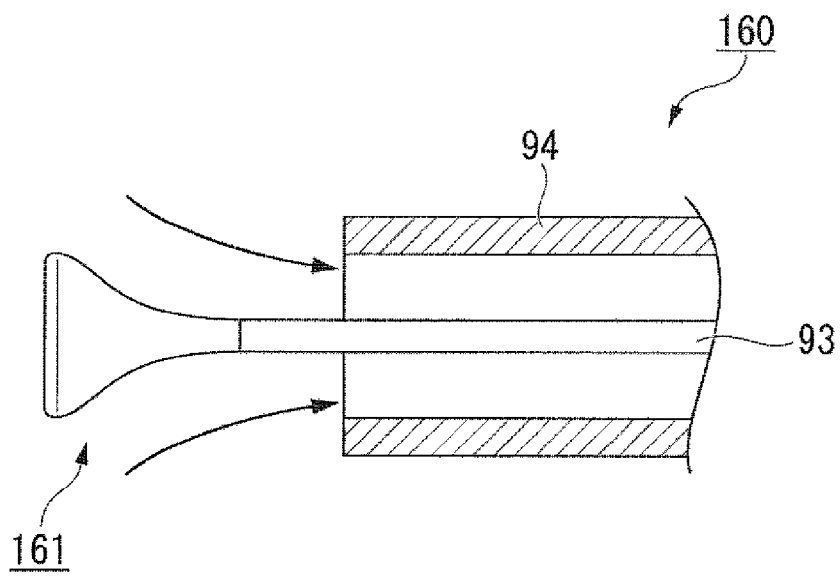
FIG. 43 is a partial cross-sectional view showing the configuration of Modified Example 7-4 of the seventh embodiment of the invention.

Next, the configuration of Modified Example 7-4 of the present embodiment will be described. FIGS. 42 and 43 are partial cross-sectional views showing the configuration of the present modified example.

As shown in FIGS. 42 and 43, a treatment instrument 160 of the present modified example is different from the above-described seventh embodiment in that this treatment instrument includes a treatment section 161 that is different from the configuration of the treatment section 91 (refer to the sixth embodiment).

The treatment section 161 of the present modified example is configured in almost the same shape as the radial cross-sectional shape of the longitudinal-axis member 94 at the distal end thereof and in a substantially conical shape that is reduced in diameter as it goes to the proximal end. In addition, in the present modified example, the slider 33-1 does not need to be provided in the operating body portion 124, and the operating wire 93 may be directly connected to the operating body portion 124.

The distal end of the treatment section 161 has a corner that is formed at an acute angle, and can scoop out a necrotic tissue or the like using the distal end of the treatment section 161.

Modified Example 7-5

Figure 44:
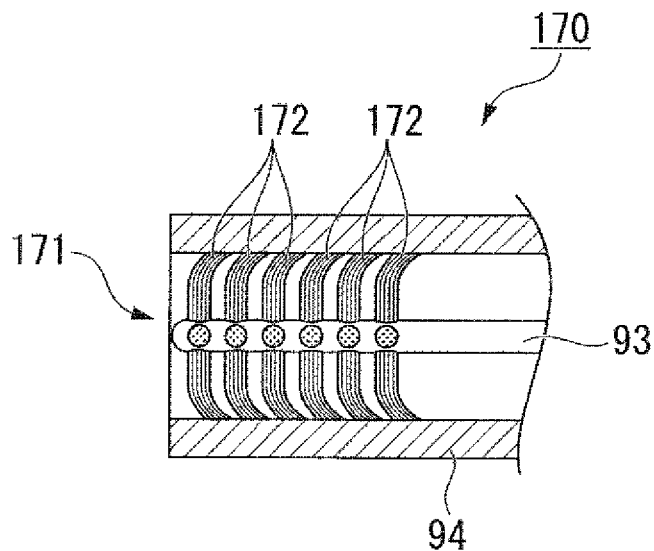
FIG. 44 is a partial cross-sectional view showing the configuration of Modified Example 7-5 of the seventh embodiment of the invention.
Figure 45:
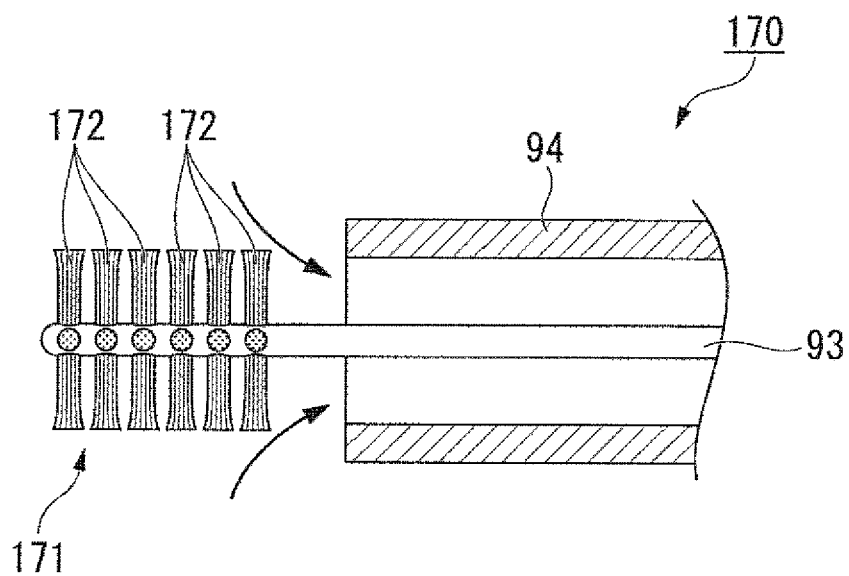
FIG. 45 is a partial cross-sectional view showing the configuration of Modified Example 7-5 of the seventh embodiment of the invention.

Next, the configuration of Modified Example 7-5 of the present embodiment will be described. FIGS. 44 and 45 are partial cross-sectional views showing the configuration of the present modified example.

As shown in FIGS. 44 and 45, a treatment instrument 170 of the present modified example is different from the above-described seventh embodiment in that this treatment instrument includes a treatment section 171 that is different from the configuration of the treatment section 91 (refer to the sixth embodiment).

The treatment section 171 of the present modified example has brush bristles 172 that extend radially outward from the outer peripheral surface of the distal end portion of the operating wire 93.

The treatment section 171 is configured in a columnar shape centered on the central axis of the operating wire 93 by protruding ends of the respective brush bristles 172. In addition, in the present modified example, the slider 33-1 does not need to be provided in the operating body portion 124, and the operating wire 93 may be directly connected to the operating body portion 124. The protruding ends of the respective brush bristles 172 touches the inner peripheral surface of the longitudinal-axis member 94 when the treatment section is housed inside the longitudinal-axis member 94. In the present modified example, a necrotic tissue can be raked out by the respective brush bristles 172.

Modified Example 7-6

Figure 46:
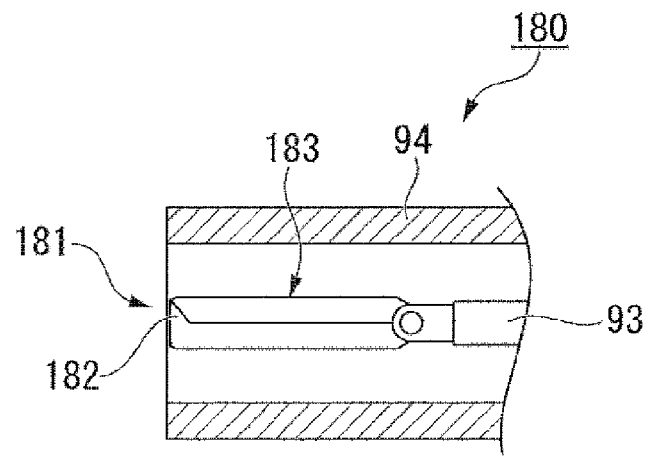
FIG. 46 is a partial cross-sectional view showing the configuration of Modified Example 7-6 of the seventh embodiment of the invention.
Figure 47:
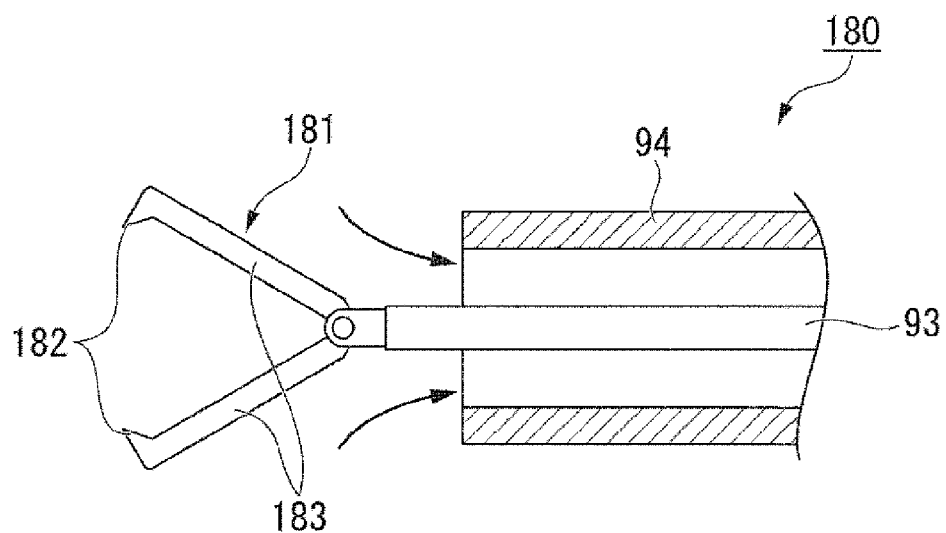
FIG. 47 is a partial cross-sectional view showing the configuration of Modified Example 7-6 of the seventh embodiment of the invention.

Next, the configuration of Modified Example 7-6 of the present embodiment will be described. FIGS. 46 and 47 are partial cross-sectional views showing the configuration of the present modified example.

As shown in FIGS. 46 and 47, a treatment instrument 180 of the present modified example is different from the above-described seventh embodiment in that this treatment instrument includes a treatment section 181 that is different from the configuration of the treatment section 91 (refer to the sixth embodiment).

The treatment section 181 of the present modified example has forceps 183 with a hook that has a pair of hooks 182 formed at the distal end thereof.

By providing the forceps 183 with a hook, the hooks 182 can be made to bite into a necrotic tissue or the like so as to reliably grip the necrotic tissue or the like.

Modified Example 7-7

Figure 48:
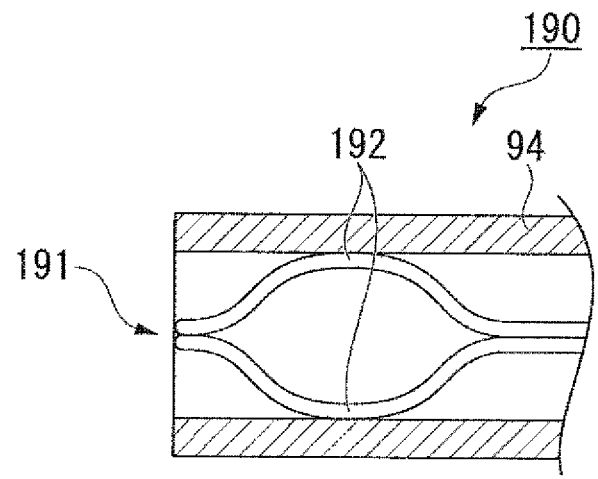
FIG. 48 is a partial cross-sectional view showing the configuration of Modified Example 7-7 of the seventh embodiment of the invention.
Figure 49:
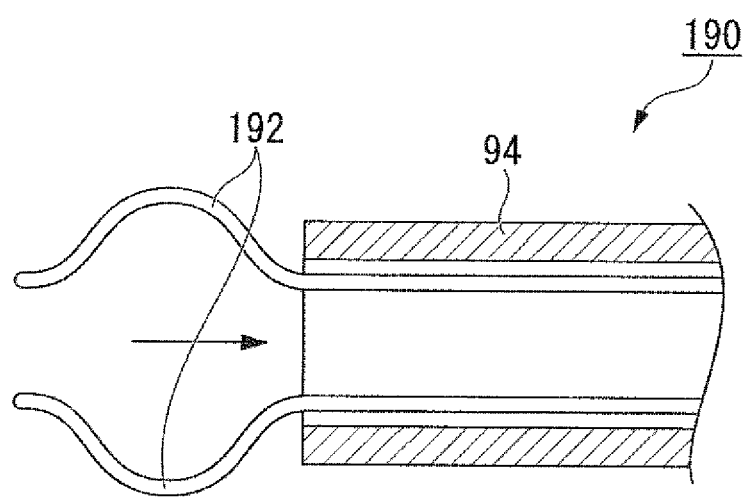
FIG. 49 is a partial cross-sectional view showing the configuration of Modified Example 7-7 of the seventh embodiment of the invention.

Next, the configuration of Modified Example 7-7 of the present embodiment will be described. FIGS. 48 and 49 are partial cross-sectional views showing the configuration of the present modified example.

As shown in FIGS. 48 and 49, a treatment instrument 190 of the present modified example is different from the above-described seventh embodiment in that this treatment instrument includes a treatment section 191 that is different from the configuration of the treatment section 91 (refer to the sixth embodiment).

The treatment section 191 of the present modified example has a pair of arms 192 that are curved so that intermediate portions of the arms swell toward the radial outside of the longitudinal-axis member 94.

Proximal ends of the pair of arms 192 are connected to the operating body portion 124, respectively. In addition, in the present modified example, the slider 33-1 does not need to be provided in the operating body portion 124, and the pair of arms 192 may be directly connected to the operating body portion 124.

The treatment instrument 190 of the present embodiment is configured so that the pair of arms 192 are opened and closed as the pair of arms 192 are advanced and retracted in the direction of the longitudinal axis of the longitudinal-axis member 94, and the external surfaces of the pair of arms 192 are pushed by the inner peripheral surfaces of the longitudinal-axis member 94.

Modified Example 7-8

Figure 50:
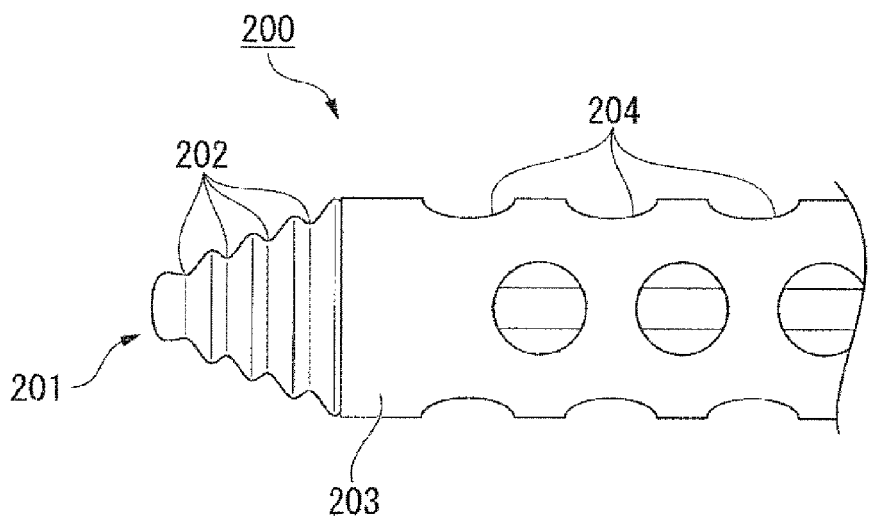
FIG. 50 is a partial cross-sectional view showing the configuration of Modified Example 7-8 of the seventh embodiment of the invention.
Figure 51:
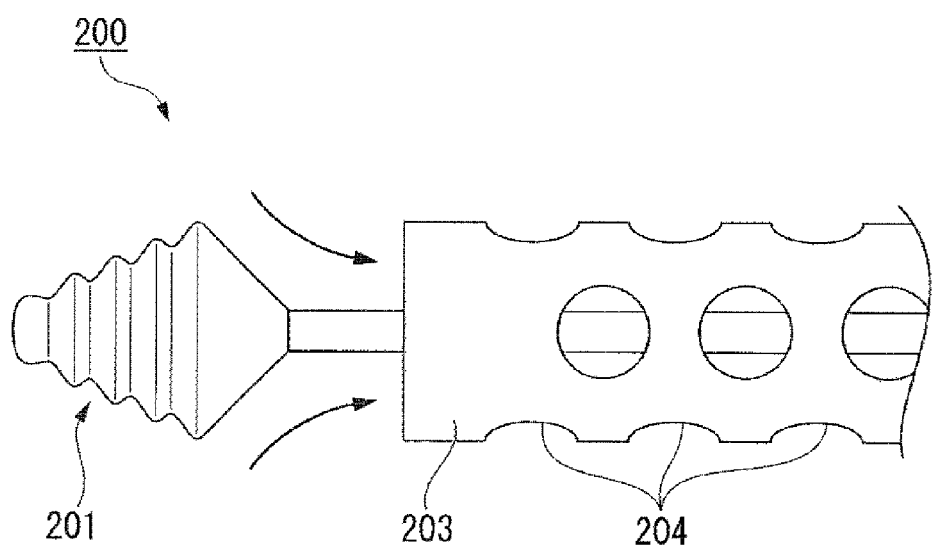
FIG. 51 is a partial cross-sectional view showing the configuration of Modified Example 7-8 of the seventh embodiment of the invention.

Next, the configuration of Modified Example 7-8 of the present embodiment will be described. FIGS. 50 and 51 are side views showing the configuration of the present modified example.

As shown in FIGS. 50 and 51, a treatment instrument 200 of the present modified example includes a treatment section 201 that is different from the configuration of the treatment section 91 (refer to the sixth embodiment), and includes a longitudinal-axis member 203 that is different from the longitudinal-axis member 94.

The treatment section 201 has a stepped portion 202 that has a concentric annular shape centered on the central axis of the operating wire 93, and has a smaller diameter gradually as it goes to the distal end side. In addition, the treatment section 201 of the present modified example may have a spiral groove whose diameter is reduced as it goes to the distal end.

Additionally, the longitudinal-axis member 203 is formed with a plurality of through holes 204 that pass through the outer wall of the distal end of the longitudinal-axis member 203. The plurality of through holes 204 are holes for suctioning a body fluid or a tissue. Additionally, the opening formed in the distal end face of the longitudinal-axis member 203, similar to the above-described respective embodiments and respective modified examples, is also an opening that enables a body fluid or a tissue to be suctioned therethrough.

In the present embodiment, the stepped portion 202 can be brought into contact with a necrotic tissue so as to scoop out the necrotic tissue. Additionally, the distal end of the longitudinal-axis member 203 can be sealed by a proximal end of the treatment section 201. If the distal end of the longitudinal-axis member 203 is sealed by the proximal end of the treatment section 201, the flow channel area on the distal end side of the longitudinal-axis member 203 becomes smaller as the opening of the distal end face of the longitudinal-axis member 203 is closed. Thereby, if the distal end face of the longitudinal-axis member 203 is closed when the inside of the longitudinal-axis member 203 is in a suction state by the suction device 100, the internal pressure of the longitudinal-axis member 203 decreases slightly.

If attachment and detachment of the proximal end side of a treatment section with respect to the distal end face of the longitudinal-axis member 203 are repeated, the pressure fluctuation inside the longitudinal-axis member 203 occurs. For example, in a case where a tissue adheres to the inside of the longitudinal-axis member 203, pressure fluctuation is caused inside the longitudinal-axis member 203, so that vibration can be transmitted to the tissue by causing, and a possibility that the tissue is removed from the inner surface of the longitudinal-axis member 203 can be enhanced.

Figure 52:
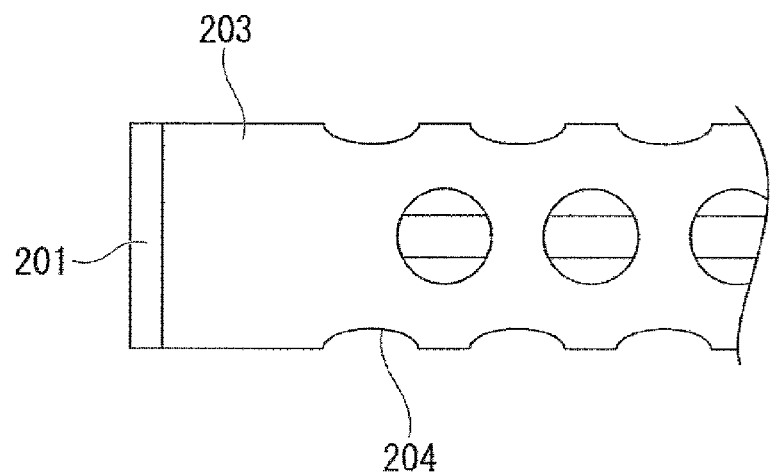
FIG. 52 is a partial cross-sectional view showing another configuration of Modified Example 7-8 of the seventh embodiment of the invention.
Figure 53:
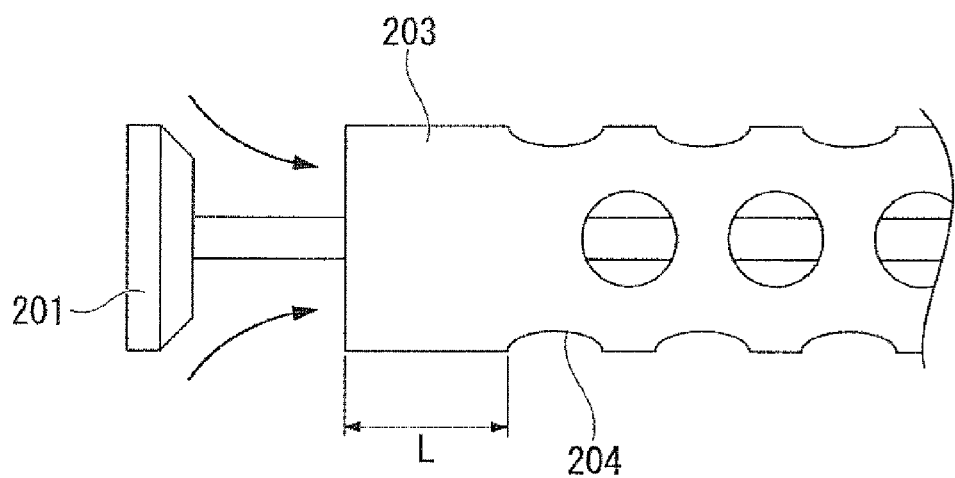
FIG. 53 is a partial cross-sectional view showing still another configuration of Modified Example 7-8 of the seventh embodiment of the invention.

In addition, as shown in FIGS. 52 and 53, the distal end side of the treatment section 201 may be flat. Additionally, the through holes 204 may be located at positions that are apart by a predetermined distance L from the distal end of the longitudinal-axis member 203 to the proximal end side.

Modified Example 7-9

Figure 54:
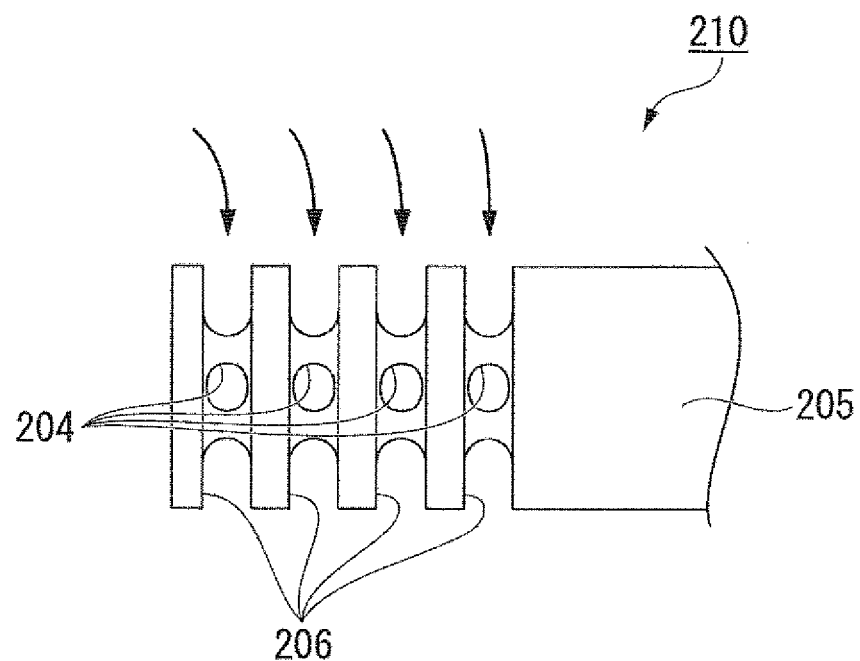
FIG. 54 is a partial cross-sectional view showing the configuration of Modified Example 7-9 of the seventh embodiment of the invention.

Next, the configuration of Modified Example 7-9 of the present embodiment will be described. FIG. 54 is a side view showing the configuration of the present modified example.

As shown in FIG. 54, a treatment instrument 210 of the present modified example is different from the configuration of the treatment instrument 200 shown in the above-described Modified Example 7-8 in that a longitudinal-axis member 205 is provided instead of the longitudinal-axis member 203.

A plurality of diameter-reduced portions 206 are provided at predetermined intervals in the direction of the central axis of the longitudinal-axis member 205 at a distal end portion of the longitudinal-axis member 205. The diameter-reduced portions 206 has a continuous groove shape in the circumferential direction of the longitudinal-axis member 205, and a plurality of through holes 204 are formed in the bottoms of the grooves.

In the present modified example, since the through holes 204 are formed in the bottoms of the grooves, the through holes 204 and a tissue can be prevented from directly contacting each other. Additionally, other tissues that are not intended to suction can be prevented from being suctioned through the through holes 204, or the longitudinal-axis member 205 can be prevented from sticking to a tissue.

While preferred embodiments of the invention have been described and illustrated above, the invention is not limited, to these embodiments. Additions, omissions, substitutions, and other modifieds of constituents can be made without departing from the concept of the present invention. Accordingly, the invention is not to be considered as being limited by the foregoing description, and is only limited by the scope of the appended claims.

For example, in the treatment instrument 1 of the first embodiment of the invention, a plurality of the volume adjusting members 12 may be provided. In a case where the plurality of volume adjusting members 12 are provided, the treatment section 2 of the treatment instrument 1 is configured in a basket shape similar to basket forceps.

What is claimed is:

1. A treatment instrument comprising:
   a longitudinal-axis member that is tubular and is provided so as to extend along a longitudinal axis;
   a collecting member that is provided at a distal end of the longitudinal-axis member, the collecting member having an opening portion for introducing a tissue and a containing portion which includes an internal space for containing the tissue and which communicates with the opening portion;
   a frame part that is provided along an edge of the opening portion in order to define a shape of the opening portion;
   an opening-closing portion that is fixed to a distal end portion of the frame part;
   an opening operating member that is connected to a proximal end portion of the frame part and is provided so as to be capable of moving inside the longitudinal-axis member along the longitudinal axis;
   a curved portion that has a first end portion fixed to the distal end portion of the frame part and a second end portion connected to the first end portion and provided to extend toward the proximal end portion of the frame part, the curved portion being formed in a curved shape through a deepest portion of the containing portion from the first end portion to the second end portion; and
   a volume operating member that is connected to the second end portion of the curved portion; wherein
      the containing portion includes a tunnel portion that has a through hole through which a part of the curved portion is configured to advance and retract;
      when the opening operating member is operated such that the opening portion defined by the frame part is opened, the volume operating member causes the curved portion to move toward a proximal end side of the longitudinal-axis member such that the containing portion is deformed in a direction approaching an opening of the opening portion, and
      the opening portion of the collecting member is closed by rotating around the opening-closing portion as a rotation center.

2. The treatment instrument according to claim 1, wherein the tunnel portion is provided in the deepest portion of the containing portion.

3. The treatment instrument according to claim 1, wherein the curved portion is a volume adjusting member that has a portion passing through the deepest portion of the containing portion, is formed in the curved shape through the deepest portion of the containing portion, and adjusts a volume of the containing portion,
   the volume operating member is provided so as to be movable along the longitudinal axis with respect to the opening operating member, and
   an operation portion allows the opening operating member and the volume operating member to be advanced and retracted in the direction of the longitudinal axis independently from each other.

4. The treatment instrument according to claim 1, wherein the curved portion is a volume adjusting member that has a portion passing through the deepest portion of the containing portion, is formed in the curved shape through the deepest portion of the containing portion, and adjusts a volume of the containing portion,
   the volume operating member is provided so as to be movable along the longitudinal axis with respect to the opening operating member, and
   (i) a depth of the containing portion when being measured in a direction intersecting an opening surface defined by the edge of the opening portion, and (ii) an opening area of the opening portion are each adjusted independently from each other by advancing and retracting the opening operating member and the volume operating member, respectively, independently from each other in the direction of the longitudinal axis.

5. The treatment instrument according to claim 4, wherein the treatment instrument has a state where the opening portion is closed when the depth of the containing portion is maintained.

6. The treatment instrument according to claim 1, wherein the curved portion is a volume adjusting member that has a portion passing through the deepest portion of the containing portion, is formed in the curved shape through the deepest portion of the containing portion, and adjusts a volume of the containing portion,
   the volume operating member that is is provided so as to be movable along the longitudinal axis with respect to the opening operating member, and
   the treatment instrument has:
      a state where a position of the opening operating member with respect to the longitudinal-axis member is fixed and the volume operating member is advanced and retracted with respect to the longitudinal-axis member, such that the volume of the containing portion varies while the opening area of the opening portion is maintained at a predetermined opening area, and
      a state where the position of the volume operating member with respect to the longitudinal-axis member is fixed and the opening operating member is advanced and retracted with respect to the longitudinal-axis member, such that the opening area of the opening portion varies while the depth of the containing portion is maintained.

7. The treatment instrument according to claim 6, wherein the treatment instrument has a state where the opening portion is closed when the depth of the containing portion is maintained.

8. The treatment instrument according to claim 5, wherein the longitudinal-axis member is a flexible structure.

9. The treatment instrument according to claim 7, wherein the longitudinal-axis member is a flexible structure.

10. The treatment instrument according to claim 1, wherein a pair of rigid portions are disposed on the opening-closing portion, each of the pair of rigid portions being formed in a rod shape, and each of the pair of rigid portions being configured to cover the distal end portion of the frame part; and a proximal end of each of the pair of rigid portions is configured to open and close by rotating around a distal end of each of the pair of rigid portions to open and close the opening portion of the collecting member.

* * * * *

UNITED STATES PATENT AND TRADEMARK OFFICE
CERTIFICATE OF CORRECTION

PATENT NO. : 9,155,551 B2
APPLICATION NO. : 13/858243
DATED : October 13, 2015
INVENTOR(S) : Noriko Kuroda et al.

It is certified that error appears in the above-identified patent and that said Letters Patent is hereby corrected as shown below:

Title Page, Item (71), Applicant, "Olympus Medical Systems Corp., Tokyo (JP)" to --Olympus Corporation, Tokyo (JP)--

Signed and Sealed this
Twenty-sixth Day of July, 2016

Michelle K. Lee
*Director of the United States Patent and Trademark Office*